United States Patent
Hou et al.

(10) Patent No.: US 11,653,609 B2
(45) Date of Patent: May 23, 2023

(54) GENERATING MAIZE PLANTS WITH ENHANCED RESISTANCE TO NORTHERN LEAF BLIGHT

(71) Applicant: PIONEER HI-BRED INTERNATIONAL, INC., Johnston, IA (US)

(72) Inventors: Zhenglin Hou, Ankeny, IA (US); April L Leonard, Des Moines, IA (US); Bailin Li, Johnston, IA (US); Girma M Tabor, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 16/903,814

(22) Filed: Jun. 17, 2020

(65) Prior Publication Data

US 2021/0000059 A1 Jan. 7, 2021

Related U.S. Application Data

(63) Continuation of application No. 15/765,566, filed as application No. PCT/US2016/057081 on Oct. 14, 2016, now abandoned.

(60) Provisional application No. 62/242,691, filed on Oct. 16, 2015.

(51) Int. Cl.
*C12N 15/82* (2006.01)
*A01H 6/46* (2018.01)
*C07K 14/415* (2006.01)

(52) U.S. Cl.
CPC ......... *A01H 6/4684* (2018.05); *C07K 14/415* (2013.01); *C12N 15/8282* (2013.01)

(58) Field of Classification Search
None
See application file for complete search history.

(56) References Cited

U.S. PATENT DOCUMENTS

| | | | |
|---|---|---|---|
| 5,844,116 A | 12/1998 | Piper | |
| 6,720,487 B1 | 4/2004 | Hoffbeck | |
| 8,062,847 B2 * | 11/2011 | Broglie | C12Q 1/6895 435/6.12 |
| 8,921,646 B2 | 12/2014 | Wilson et al. | |
| 9,040,772 B2 | 5/2015 | Li et al. | |
| 2010/0095395 A1 | 4/2010 | Wilson | |
| 2015/0315605 A1 | 11/2015 | Li et al. | |
| 2021/0274739 A1 * | 9/2021 | Hou | C12N 15/8282 |
| 2022/0275392 A1 | 9/2022 | Gao et al. | |

FOREIGN PATENT DOCUMENTS

| | | |
|---|---|---|
| WO | 2008/021225 A2 | 2/2008 |
| WO | 2010045211 A2 | 4/2010 |
| WO | 2011/163590 A1 | 12/2011 |
| WO | 2014/036048 A1 | 3/2014 |
| WO | 2015026883 A1 | 2/2015 |
| WO | 2015026886 A1 | 2/2015 |
| WO | 2016040030 A1 | 3/2016 |
| WO | 2021257206 A1 | 12/2021 |

OTHER PUBLICATIONS

Zuo et al. Nature Genetics (2015) 47(2): 151-158.*
Qin, Yang et al., "Quantitative Disease Resistance: Dissection and Adoption in Maize"; Molecular Plant; Mar. 2017; vol. 10; pp. 402-413.
Schnable, P. S., et al.: "The B73 Maize Genome: Complexity, Diversity, and Dynamics", Science Magazine (2009) vol. 326, No. 5956, pp. 1112-1115.
UniProt Database Accession No. UPI000220E9DC dated Mar. 19, 2013.
Yang, et al.: "Quantitative Disease Resistance: Dissection and Adoption in Maize," Molecular Plant, vol. 10, pp. 402-413.
International Search Report and Written Opinion, International Application No. PCT/US2016/057081 dated Aug. 2, 2017.
Hurni, Severine, et al.: "The maize disease resistance gene Htn1 against northern corn leaf blight encodes a wall-associated receptor-like kinase", PNAS Proceedings of the National Academy of Sciences, Jul. 14, 2015 (Jul. 14, 2015), vol. 112, No. 28. pp. 8780-8785.
Li, L. J.; et al.: "The physical location of the gene ht1 (Helminthosporium turcium resistance1) in maize (Zea mays L.)", Hereditas, 1998, vol. 129, pp. 101-106.
Shi, Jinrui, et al.: "ARGOS8 variants generated by CRISPR-CAS9 improve maize grain yield under field drought stress conditions", Plant Biotechnology Journal, Aug. 17, 2016 (Aug. 17, 2016), vol. 15, No. 2, pp. 207-216.
International Search Report and Written Opinion for International Application No. PCT/US2017/055835, dated Mar. 13, 2018.
Non-Final Office Action for U.S. Appl. No. 17/319,319, dated Sep. 22, 2022.

* cited by examiner

*Primary Examiner* — Medina A Ibrahim

(57) ABSTRACT

Compositions and methods for generating maize plants that exhibit resistance to northern leaf blight are provided herein. Isolated polynucleotides encoding a polypeptide that confers resistance to northern leaf blight, polynucleotide constructs comprising such, and maize plants comprising the polynucleotide constructs are provided. The methods include expressing an isolated polynucleotide in a maize cell via standard transformation methods and obtaining a maize plant from said maize cell.

19 Claims, 4 Drawing Sheets

Specification includes a Sequence Listing.

FIGURE 1A

```
1    MENPDAQAKAWAAEMRELAYDMEDSIDLFTHHVDHEPADTATTGVKRFFLRIIRKLKKLH  SEQ ID NO 2
1    MENPDAQAKAWAAEMRELAYDMEDSIDLFTHHVDHEPADTATTGVKRFFLRIIRKLKKLH  SEQ ID NO 4
1    MENPDAQAKAWAAEMRELAYDMEDSIDLFTHHVDHEPADTATTGVKRFFLRIIRKLKKLH  SEQ ID NO 6
1    MENPDAQAKAWAAEMRELAYDMEDSIDLFTHHVDHEPADTATTGVKRFFLRIIRKLKKLH  SEQ ID NO 8

61   YRHRFVQEIKQLHDLANESYRRRKRYRIEEGGSSLSHAEIDPRLEALYVEVEKLVGIQGP  SEQ ID NO 2
61   YRHRFVQEIKQLHDLANESYRRRKRYRIEEGGSSLSHAEIDPRLEALYVEVEKLVGIQGP  SEQ ID NO 4
61   YRHRFAQEIKQLHDLANESYRRRKRYRIEEGGSSLPHAEIDPRLEALYVEVEKLVGIQGP  SEQ ID NO 6
61   YRHRFAQEIKQLHDLANESYRRRKRYRIEEGGSSLPHAEIDPRLEALYVEVEKLVGIQGP  SEQ ID NO 8

121  SQEIIGQLVGENAAERRVVAVGSGGSGKTTLAKQVYEKIRCQFSCAAFVSVSQKPNMN  SEQ ID NO 2
121  SQEIIGQLVGENAAERRVVAVGSGGSGKTTLAKQVYEKIRCQFSCAAFVSVSQKPNMN  SEQ ID NO 4
121  SQEIIGQLVGENAAERRVVAVGSGGSGKTTLAKQVYEKIRCQFSCAAFVSVSQKPNMN  SEQ ID NO 6
121  SQEIIGQLVGENAAERRVVAVGSGGSGKTTLAKQVYEKIRCQFSCAAFVSVSQKPNMN  SEQ ID NO 8

181  SLLWELLSQIGNHGGDLGMMAVGYCSDKQLIDRLRSHLEKQ----------RYLVVID  SEQ ID NO 2
181  SLLWELLSQIGNHGGDLGMMAVGYCSDKQLIDRLRSHLEKQ----------RYLVVID  SEQ ID NO 4
181  SLLWELLSQIGNHGGDLGMMAVGYCSDKQLIDRLRSHLEKQ----------RYLVVID  SEQ ID NO 6
181  SLLWELLSQIGNHGGDLGMMAVGYCSDKQLIDRLRSHLEKQRTDFSTASQSALRYLVVID  SEQ ID NO 8
```

FIGURE 1B

```
229 DVWTNSAWETIQCALPKNAHASKILLTTRINSVGQFSCTPDEGFIYQMKPLCRNDSENLF  SEQ ID NO 2
229 DVWTNSAWETIQCALPKNAHASKILLTTRINSVGQFSCTPDEGFIYQMKPLCRNDSENLF  SEQ ID NO 4
229 DVWTNSAWETIQCALPKNAHASKILLTTRINSVGQFSCTPDEGFIYQMKPLCRNDSENLF  SEQ ID NO 6
241 DVWTNSAWETIQCALPKNAHASKILLTTRINSVGQFSCTPDEGFIYQMKPLCRNDSENLF  SEQ ID NO 8

289 LKRTLCDKDKFPAQLEGIKNEIEKCDGLPLAIVTLASMLATKQRTREEWERALDSIHSM   SEQ ID NO 2
289 LKRTLCDKDKFPAQLEGIKNEIEKCDGLPLAIVTLASMLATKQRTREEWERALDSIHSM   SEQ ID NO 4
289 LKRTLCDKDKFPAQLEGIKNEIEKCDGLPLAIVTLASMLATKQRTREEWERALDSIHST   SEQ ID NO 6
301 LKRTLCDKDKFPAQLEGIKNEIEKCDGLPLAIVTLASMLATKQRTREEWERALDSIHST   SEQ ID NO 8

349 HKKDSGLEVMDKILSLSYRDLPHNMRNCLLYLSTFPEDHTIYKDALVWRWMAEGFIAETQ  SEQ ID NO 2
349 HKKDSGLEVMDKILSLSYRDLPHNMRNCLLYLSTFPEDHTIYKDALVWRWMAEGFIAETQ  SEQ ID NO 4
349 HKKDSSLEVMDKILSLSYRDLPHNMRNCLLYISTFPEDHTIYKDALVWRWMAEGFIAETQ  SEQ ID NO 6
361 HKKDSSLEVMDKILSLSYRDLPHNMRNCLLYISTFPEDHTIYKDALVWRWMAEGFIAETQ  SEQ ID NO 8

409 GFTLEQVAEGYFYEFVNRSLVQPITLRSRYEMRGEGGCRVHDIVLNFLISRAAEENFLTT  SEQ ID NO 2
409 GFTLEQVAEGYFYEFVNRSLVQPITLRSRYEMRGEGGCRVHDIVLNFLISRAAEENFLTT  SEQ ID NO 4
409 GFTLEQVAEGYFYEFVNRSLVQPITLRSRYEMRGEGGCRVHDIVLNFLISRAAEENFLTT  SEQ ID NO 6
421 GFTLEQVAEGYFYEFVNRSLVQPITLRSRYEMRGEGGCRVHDIVLNFLISRAAEENFLTT  SEQ ID NO 8
```

FIGURE 1C

```
469 LYGAQGVPSSDRRIRRLSVWDSPEHALAVSRATMNLSHLRSVRICNVGDWPVPAVLDLPV  SEQ ID NO 2
469 LYGAQGVPSSDRRIRRLSVWDSPEHALAVSRATMNLSHLRSVRICNVGDWPVPAVLDLPV  SEQ ID NO 4
469 LYGAQGVPSSDRRIRRLSVWDSPEHALAVSRATMNLSHLRSVRICNVGDWPVPAVLDLPV  SEQ ID NO 6
481 LYGAQGVPSSDRRIRRLSVWDSPEHALAVSRATMNLSHLRSVRICNVGDWPVPAVLDLPV  SEQ ID NO 8

529 LRVLDLEGCRDLRIDEPDCILSLFHLRYLGFRSASGVVLPAQIGNLHHLQTIDLSGTGVT  SEQ ID NO 2
529 LRVLDLEGCRDLRIDEPDCILSLFHLRYLGFRSASGVVLPAQIGNLHHLQTIDLSGTGVT  SEQ ID NO 4
529 LRVLDLEGCRDLRIVDPDCILSLFHLRYLGFRSASGVVLPAQIGNLHHLQTIDLSGTGVT  SEQ ID NO 6
541 LRVLDLEGCRDLRIVDPDCILSLFHLRYLGFRSASGVVLPAQIGNLHHLQTIDLSGTGVT  SEQ ID NO 8

589 QLPESIVQLKRLMHLVGQRLIMPDGFGSMESLEELGTIDCCKCP|VSFGEDLALLSRLRVL  SEQ ID NO 2
589 QLPESIVQLKRLMHLVGQRLIMPDGFGSMESLEELGTIDCCKCP|VSFGEDLALLSRLRVL  SEQ ID NO 4
589 QLPESIVQLKRLMHLVGQRLIMPDGFGSMESLEELGTIDCCKCP|AEG--------APSD  SEQ ID NO 6
601 QLPESIVQLKRLMHLVGQRLIMPDGFGSMESLEELGTIDCCKCP|AEG--------APSD  SEQ ID NO 8

649 RVAFIGVETSDMETRRKSLMSSLCKLGGDNLRRVTIIDLAGGGDCFVESWHPPPRLLQKF  SEQ ID NO 2
649 RVAFIGVETSDMETRRKSLMSSLCKLGGDNLRRVTIIDLAGGGDCFVESWHPPPRLLQKF  SEQ ID NO 4
640 RVAFVGVETSDMETRRKSLMSSLCKLGGDNLRRVTIIDLAGGGDCFVESWHPPPRLLQKF  SEQ ID NO 6
652 RVAFVGVETSDMETRRKSLMSSLCKLGGDNLRRVTIIDLAGGGDCFVESWHPPPRLLQKF  SEQ ID NO 8
```

FIGURE 1D

```
709 IHISQQQHFSRFPEWISSCLCDLTHLDIKAEKMEREHLSVLEHLPAIRCLYLFVKRVSED  SEQ ID NO 2
709 IHIS--QHFSRFPEWISSCLCDLTHLDIKAEKMEREHLSVLEHLPAIRCLYLFVKRVSED  SEQ ID NO 4
700 IHISQQQHFSRFPEWISSCLCDLTHLDIKAEKMEREHLSVLEHLPAIRYLYLFVKRVSED  SEQ ID NO 6
712 IHISQQQHFSRFPEWISSCLCDLTHLDIKAEKMEREHLSVLEHLPAIRYLYLFVKRVSED  SEQ ID NO 8

769 GLAISHGAFRCLRRLEFCNVDGPGLMFAGGVPMLEWLRLGFDADRAQSTYGGLEVGIQRL  SEQ ID NO 2
767 GLVISHGAFRCLRRLEFCNVDGPGLMFAGGVPMLEWLRLGFDADRAQSTYGGLEVGIQRL  SEQ ID NO 4
760 GLVISHSAFRCLRRLEFCNLDGPGLMFAGGVPMLEWLRLGFDADRAQSTYGGLEVGIQRL  SEQ ID NO 6
772 GLVISHSAFRCLRRLEFCNLDGPGLMFAGGVPMLEWLRLGFDADRAQSTYGGLEVGIQRL  SEQ ID NO 8

829 SSLKHVVLIVWMVSEGGDDPAEQAVWSAINGQVEMLPNSPTVDIRFRRRSQLQASSE.  SEQ ID NO 2
827 SSLKHVVLIVWMVSEGGDDPAEQAVWSAINGQVEMLPNSPTVDIRFRRRSQLQASSE.  SEQ ID NO 4
820 SSLKHVVLIVCMVSEGGDDPAEQAVWSAINGQVEMLPNSPTVDIRFRRRSQLQASSE.  SEQ ID NO 6
832 SSLKHVVLIVCMVSEGGDDPAEQAVWSAINGQVEMLPNSPTVDIRFRRRSQLQASSE.  SEQ ID NO 8
```

GENERATING MAIZE PLANTS WITH ENHANCED RESISTANCE TO NORTHERN LEAF BLIGHT

CROSS REFERENCE TO RELATED APPLICATIONS

This application claims the benefit of U.S. Provisional Application No. 62/242,691, filed Oct. 16, 2015, the entire contents of which are hereby incorporated by reference.

FIELD

The present disclosure relates to compositions and methods useful in generating maize plants with enhanced resistance to northern leaf blight.

REFERENCE TO SEQUENCE LISTING SUBMITTED ELECTRONICALLY

The official copy of the sequence listing is submitted electronically via EFS-Web as an ASCII formatted sequence listing with a file named 20160928_BB2396PCT_SequenceListing.txt created on Sep. 28, 2016 and having a size 65 kilobytes and is filed concurrently with the specification. The sequence listing contained in this ASCII formatted document is part of the specification and is herein incorporated by reference in its entirety.

BACKGROUND

Northern leaf blight (NLB), induced by the fungal pathogen *Exserohilum turcicum* (previously called *Helminthosporium turcicum*), is a serious foliar wilt disease of maize in many tropical and temperate environments. Symptoms can range from cigar-shaped lesions on the lower leaves to complete destruction of the foliage, thereby reducing the amount of leaf surface area available for photosynthesis. A reduction in photosynthetic capability leads to a lack of carbohydrates needed for grain fill, which impacts grain yield. Mid-altitude regions of the tropics, about 900-1600 m above sea level, have a particularly favorable climate for northern leaf blight, as dew periods are long and temperatures moderate. However, northern leaf blight can also yield losses of 30-50% in temperate environments, such as in the United States, during wet seasons, particularly if the infection is established on the upper leaves of the plant by the silking stage.

The most effective and most preferred method of control for northern leaf blight is the planting of resistant hybrids. Several varieties or races of *Exserohilum turcicum* are present in nature, leaving growers with two hybrid options: partial resistant hybrids, which offer low-level, broad spectrum protection against multiple races, and race-specific resistant hybrids, which protect against a specific race. Genetic sources of resistance to *Exserohilum turcicum* have been described, and four *Exserohilum turcicum* resistance loci have been identified: Ht1, Ht2, Ht3, and Htn1. Gene Ht1 maps to the long arm of chromosome 2 where it is closely linked to umc36 (Coe, E. H. et al. (1988), *Corn and Corn Improvement*, 3rd edn., pp. 81-258), sgcr506 (Gupta, M. et al. (1989) *Maize Genet. Coop. Newsl.* 63, 112), umc150B (Bentolila, S. et al. (1991) *Theor. Appl. Genet.*, 82:393-398), and pic18a (Collins et al. (1998) *Molecular Plant-Microbe Interactions*, 11:968-978), and it is closely flanked by umc22 and umc122 (Li et al. (1998) *Hereditas*, 129:101-106). Gene Ht2 maps to the long arm of chromosome 8 in the umc48-umc89 interval (Zaitlin et al. (1992) *Maize Genet. Coop. Newsl.*, 66, 69-70), and gene Ht3 maps to chromosome 7 near bnlg1666 (Van Staden, D et al. (2001) *Maize Genetics Conference Abstracts* 43:P134). The Htn1 gene maps to chromosome 8, approximately 10 cM distal to Ht2 and 0.8 cM distal to the RFLP marker umc117 (Simcox and Bennetzen (1993) *Maize Genet. Coop. Newl.* 67, 118-119; Simcox and Bennetzen (1993) *Phytopathology*, 83:1326-1330).

The methods of controlling northern leaf blight by reducing fungal inoculum require additional time and resources on the part of the farmer, and in addition, can have detrimental effects on the environment. This makes the planting of resistant hybrids even more attractive to farmers and the general public. Thus, it is desirable to provide compositions and methods for generating maize plants with enhanced resistance to northern leaf blight.

SUMMARY

Presented herein are compositions and methods for generating maize plants exhibiting resistance to northern leaf blight, whether that resistance is newly conferred or enhanced.

Isolated polynucleotides are presented herein that can be used to generate maize plants that exhibit resistance to northern leaf blight. An isolated polynucleotide may be selected from the group consisting of: (a) the nucleotide sequence set forth in SEQ ID NO:1 (PH4GP c-DNA), SEQ ID NO:3 (PH1W2 cDNA), or SEQ ID NO:9 (PH4GP Genomic sequence); (b) a nucleotide sequence encoding a CC-NB-LRR polypeptide having an amino acid sequence of at least 90% sequence identity when compared to SEQ ID NO:2 or SEQ ID NO:4, based on the CLUSTAL W method of alignment with default parameters; (c) a nucleotide sequence encoding a CC-NB-LRR polypeptide having an amino acid sequence of at least 90% sequence identity when compared to SEQ ID NO:2 or SEQ ID NO:4, based on the CLUSTAL W method of alignment with default parameters, wherein said polypeptide comprises the amino acid sequence set forth in SEQ ID NO:10; and (d) a nucleotide sequence encoding a CC-NB-LRR polypeptide having the sequence set forth in SEQ ID NO:2 or SEQ ID NO:4.

Polynucleotide constructs comprising the isolated polynucleotides are also provided, wherein an isolated polynucleotide is operably linked to a promoter. A polynucleotide construct may further comprise one or more heterologous nucleic acid sequences that encode a polypeptide selected from the group consisting of: a polypeptide conferring disease resistance, a polypeptide conferring herbicide resistance, a polypeptide conferring insect resistance, a polypeptide involved in carbohydrate metabolism, a polypeptide involved in fatty acid metabolism, a polypeptide involved in amino acid metabolism, a polypeptide involved in plant development, a polypeptide involved in plant growth regulation, a polypeptide involved in yield improvement, a polypeptide involved in drought resistance, a polypeptide involved in cold resistance, a polypeptide involved in heat resistance, and/or a polypeptide involved in salt resistance, wherein the one or more heterologous nucleic acid sequences are operably linked to a promoter. For example, a polypeptide conferring disease resistance may be a polypeptide that confers resistance to northern leaf blight (NLB), which may further have an amino acid sequence of at least 90% sequence identity when compared to SEQ ID NO:11 or 12, based on the CLUSTAL W method of alignment with default parameters.

Maize plant cells comprising the polynucleotide constructs and maize plants comprising the maize plant cells are also provided.

Methods for generating maize plants that exhibit resistance to northern leaf blight are provided herein, in which a polynucleotide construct comprising an isolated polynucleotide provided herein, wherein said isolated polynucleotide is operably linked to at least one regulatory sequence, is expressed in a regenerable maize plant cell, and a maize plant that exhibits resistance to northern leaf blight is generated from the maize plant cell. The maize plant generated by the method comprises in its genome the polynucleotide construct. The regulatory sequence may be a promoter and/or a terminator and may be native to maize. In some aspects, the regulatory sequence is native to the Ht1 gene. In still other aspects, the polynucleotide construct comprises one or more additional heterologous nucleic acid sequences that encode a polypeptide selected from the group consisting of: a polypeptide conferring disease resistance, a polypeptide conferring herbicide resistance, a polypeptide conferring insect resistance, a polypeptide involved in carbohydrate metabolism, a polypeptide involved in fatty acid metabolism, a polypeptide involved in amino acid metabolism, a polypeptide involved in plant development, a polypeptide involved in plant growth regulation, a polypeptide involved in yield improvement, a polypeptide involved in drought resistance, a polypeptide involved in cold resistance, a polypeptide involved in heat resistance, and/or a polypeptide involved in salt resistance, wherein each heterologous nucleic acid sequence is operably linked to a promoter. The polypeptide may be one that confers resistance to northern leaf blight (NLB), such as for example, a polypeptide having an amino acid sequence of at least 90% sequence identity when compared to SEQ ID NO:11 or 12, based on the CLUSTAL W method of alignment with default parameters. A progeny plant comprising the polynucleotide construct may also be generated by crossing the maize plant generated by the method to a second maize plant that does not comprise in its genome the polynucleotide construct.

BRIEF DESCRIPTION OF THE DRAWINGS AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

FIGS. 1A-1D show the alignment of the CC-NB-LRR variants from PH4GP (SEQ ID NO:2), PH1W2 (SEQ ID NO:4), and B73 (SEQ ID NOs:6 and 8). The deletion in the LRR region in the B73 alleles is boxed in FIG. 1C.

SEQ ID NO:1 is the nucleotide sequence of the Ht1 cDNA found in inbred line PH4GP.

SEQ ID NO:2 is the amino acid sequence of the polypeptide encoded by SEQ ID NO:1.

SEQ ID NO:3 is the nucleotide sequence of the Ht1 cDNA found in inbred line PH1W2.

SEQ ID NO:4 is the amino acid sequence of the polypeptide encoded by SEQ ID NO:3.

SEQ ID NO:5 is the nucleotide sequence of the Ht1 cDNA found in inbred line B73 and herein referred to as the "B73-high allele".

SEQ ID NO:6 is the amino acid sequence of the polypeptide encoded by SEQ ID NO:5.

SEQ ID NO:7 is the nucleotide sequence of the Ht1 cDNA found in inbred line B73 and herein referred to as the "B73-low allele".

SEQ ID NO:8 is the amino acid sequence of the polypeptide encoded by SEQ ID NO:7.

SEQ ID NO:9 is the nucleotide sequence of the Ht1 genomic DNA found in inbred line PH4GP.

SEQ ID NO:10 is the amino acid sequence of a region found in the Ht1 polypeptides of resistant alleles.

SEQ ID NO:11 is the amino acid sequence of NLB18 from line PH99N in patent application WO2011163590.

SEQ ID NO:12 is the amino acid sequence of NLB18 from line PH26N in patent application WO2011163590.

DETAILED DESCRIPTION

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

I. Compositions

A. Ht1 Polynucleotides and Polypeptides

Mapping of a QTL associated with northern leaf blight resistance on chromosome 2, using a population derived from a cross between northern leaf blight resistant line PH4GP and northern leaf blight susceptible line PH5W4, was described in US2010095395. Presented herein is the cloning of the Ht1 gene in maize and identification of a putative CC-NB-LRR (coiled-coil, nucleotide-binding, leucine-rich repeat) gene as the causal gene. Ht1 cDNA sequences from PH4GP and PH1W2, the two resistant sources described in US2010095395, are represented by SEQ ID NOs:1 and 3, respectively, while the amino acid sequences of the encoded polypeptides are represented by SEQ ID NO:2 and 4. Moreover, a construct containing the genomic sequence of the PH4GP (resistant) allele (SEQ ID NO:9) was generated and transformed into a susceptible transformation line using *Agrobacterium*-mediated transformation, resulting in maize plants with resistance to northern leaf blight.

The *Zea mays* CC-NB-LRR (coiled-coil, nucleotide-binding, leucine-rich repeat; also referred to as Ht1) gene is a member of a large and complex family of disease resistance genes. The mechanism of NB-LRR protein activation and subsequent signaling in effector triggered immunity is not well understood (Eitas and Dangl. 2010. *Curr Opin Plant Biol* 13(4):472-477).

Thus, presented herein are polynucleotides that can be used to generate maize plants with resistance to northern leaf blight. The polynucleotide may be (a) the nucleotide sequence set forth in SEQ ID NO:1 (PH4GP c-DNA), SEQ ID NO:3 (PH1W2 cDNA), or SEQ ID NO:9 (PH4GP Genomic sequence); (b) a nucleotide sequence encoding a CC-NB-LRR polypeptide having an amino acid sequence of at least 90%, 91%, 92%, 93%, 94%, 95%, 96%, 97%, 98%, or 99% sequence identity when compared to SEQ ID NO:2 or SEQ ID NO:4, based on the CLUSTAL W method of alignment with default parameters; (c) a nucleotide sequence encoding a CC-NB-LRR polypeptide having an amino acid sequence of at least 90%, 91%, 92%, 93%, 94%, 95%, 96%, 97%, 98%, or 99% sequence identity when compared to SEQ ID NO:2 or SEQ ID NO:4, based on the CLUSTAL W method of alignment with default parameters, wherein said polypeptide comprises the amino acid sequence set forth in SEQ ID NO:10, which is the sequence of the deleted region of Ht1 in B73; and (d) a nucleotide sequence encoding a CC-NB-LRR polypeptide having the sequence set forth in SEQ ID NO:2 or SEQ ID NO:4.

The use of the term "polynucleotide" is not intended to limit a polynucleotide of the disclosure to a polynucleotide comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the disclosure also encompass all forms of sequences including, but not limited to, single-stranded forms, double-stranded forms, hairpins, stem-and-loop structures, and the like.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For purposes of this disclosure, "isolated" or "recombinant" when used to refer to nucleic acid molecules excludes isolated unmodified chromosomes. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the polypeptide of the disclosure or a biologically active portion thereof is recombinantly produced, optimally culture medium represents less than about 30%, 20%, 10%, 5%, or 1% (by dry weight) of chemical precursors or non-protein-of-interest chemicals.

As used herein, a "recombinant" polynucleotide comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest such that an additional chemically linked nucleic acid segment is located either 5', 3' or internal to the polynucleotide of interest. Alternatively, the chemically-linked nucleic acid segment of the recombinant polynucleotide can be formed by the deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence.

A "recombinant polypeptide" comprises a combination of two or more chemically linked amino acid segments which are not found directly joined in nature. In specific embodiments, the recombinant polypeptide comprises an additional chemically linked amino acid segment that is located either at the N-terminal, C-terminal or internal to the recombinant polypeptide. Alternatively, the chemically-linked amino acid segment of the recombinant polypeptide can be formed by deletion of at least one amino acid. The additional chemically linked amino acid segment or the deleted chemically linked amino acid segment can be of any length, including for example, 1, 2, 3, 4, 5, 6, 7, 8, 9, 10, 15, 20 or amino acids.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the CLUSTAL V method of alignment (Higgins and Sharp, CABIOS. 5:151 153 (1989)) with the default parameters (GAP PENALTY=10, GAP LENGTH PENALTY=10). Default parameters for pairwise alignments and calculation of percent identity of protein sequences using the CLUSTAL V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the CLUSTAL V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

B. Polynucleotide Constructs

The Ht1 polynucleotides disclosed herein can be provided in expression cassettes (such as, for example, in the form of polynucleotide constructs) for expression in the plant of interest or any organism of interest. The cassette can include 5' and 3' regulatory sequences operably linked to an Ht1 polynucleotide. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the Ht1 polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), an Ht1 polynucleotide, and a transcriptional and translational termination region (i.e., termination region) functional in plants. The regulatory regions (i.e., promoters, transcriptional regulatory regions, and translational termination regions) and/or the Ht1 polynucleotide may be native/analogous to the maize plant cell or to each other. Alternatively, the regulatory regions and/or the Ht1 polynucleotide may be heterologous to the maize plant cell or to each other.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The termination region may be native with the transcriptional initiation region, may be native with a maize plant, or may be derived from another source (i.e., foreign or heterologous) with respect to the promoter, the Ht1 polynucleotide, the maize plant, or any combination thereof.

The expression cassettes may additionally contain 5' leader sequences. Such leader sequences can act to enhance translation. Translation leaders are known in the art and include viral translational leader sequences.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used to express the various Ht1 sequences disclosed herein, including the native promoter of the polynucleotide sequence of interest (such as, for example, the native promoter of the Ht1 gene). The promoters can be selected based on the desired outcome. Such promoters include, for example, constitutive, inducible, tissue-preferred, or other promoters for expression in plants or in any organism of interest. Synthetic promoters can also be used to express Ht1 sequences. Synthetic promoters include for example a combination of one or more heterologous regulatory elements.

A polynucleotide construct may be a recombinant DNA construct. A "recombinant DNA construct" comprises two or more operably linked DNA segments which are not found operably linked in nature. Non-limiting examples of recombinant DNA constructs include a polynucleotide of interest operably linked to heterologous sequences which aid in the expression, autologous replication, and/or genomic insertion of the sequence of interest. Such heterologous and operably linked sequences include, for example, promoters, termination sequences, enhancers, etc, or any component of an expression cassette; a plasmid, cosmid, virus, autonomously replicating sequence, phage, or linear or circular single-stranded or double-stranded DNA or RNA nucleotide sequence; and/or sequences that encode heterologous polypeptides.

C. Maize Plant Cells and Maize Plants

"Maize" refers to a plant of the *Zea mays* L. ssp. *mays* and is also known as "corn".

Maize plants, maize plant cells, maize plant parts and seeds, and maize grain having the Ht1 sequences disclosed herein are also provided. In specific embodiments, the plants and/or plant parts have stably incorporated at least one heterologous Ht1 polypeptide disclosed herein. In addition, the plants or organism of interest can comprise multiple Ht1 polynucleotides (i.e., at least 1, 2, 3, 4, 5, 6 or more).

As used herein, the term maize plant includes maize plant cells, maize plant protoplasts, maize plant cell tissue cultures from which maize plants can be regenerated, maize plant calli, maize plant clumps, and maize plant cells that are intact in maize plants or parts of maize plants such as embryos, pollen, ovules, seeds, leaves, flowers, kernels, ears, cobs, husks, stalks, roots, root tips, anthers, and the like. Grain is intended to mean the mature seed produced by commercial growers for purposes other than growing or reproducing the species.

D. Other Traits of Interest

In some embodiments, the Ht1 polynucleotides disclosed herein may be engineered into a molecular stack. Thus, the various maize plants, maize plant cells and maize seeds disclosed herein can further comprise one or more traits of interest, and in more specific embodiments, the maize plant, maize plant part or maize plant cell is stacked with any combination of polynucleotide sequences of interest in order to create plants with a desired combination of traits.

As used herein, the term "stacked" includes having the multiple traits present in the same plant or organism of interest. In one non-limiting example, "stacked traits" comprise a molecular stack where the sequences are physically adjacent to each other. A trait, as used herein, refers to the phenotype derived from a particular sequence or groups of sequences.

A polynucleotide DNA construct described herein may also comprise one or more heterologous nucleic acid sequences that encode a polypeptide selected from the group consisting of: a polypeptide conferring disease resistance, a polypeptide conferring herbicide resistance, a polypeptide conferring insect resistance, a polypeptide involved in carbohydrate metabolism, a polypeptide involved in fatty acid metabolism, a polypeptide involved in amino acid metabolism, a polypeptide involved in plant development, a polypeptide involved in plant growth regulation, a polypeptide involved in yield improvement, a polypeptide involved in drought resistance, a polypeptide involved in cold resistance, a polypeptide involved in heat resistance, and/or a polypeptide involved in salt resistance, wherein each heterologous nucleic acid sequence is operably linked to a promoter.

A polypeptide conferring disease resistance may be another polypeptide that confers resistance to northern leaf blight (NLB). For example, a polynucleotide DNA construct may comprise a resistant allele of Ht1 and a resistant allele of NLB18 (in WO2011163590). The amino acid sequence of the NLB18 polypeptide from line PH99N is presented herein as SEQ ID NO:11; the amino acid sequence of the NLB18 polypeptide from line PH26N is presented herein as SEQ ID NO:12. Both PH99N and PH26N are maize lines showing resistance to northern leaf blight that reflect different sources of resistance with respect to the chromosome 8 QTL, as described in application WO2011163590. A resistant allele of NLB18 may encode a polypeptide having an amino acid sequence of at least 90%, 91%, 92%, 93%, 94%, 95%, 96%, 97%, or 99% sequence identity when compared to SEQ ID NO:11 or 12, based on the CLUSTAL W method of alignment with default parameters.

II. Methods of Generating Maize Plants with Northern Leaf Blight Resistance

"*Exserohilum turcicum*", previously referred to as *Helminthosporium turcicum*, is the fungal pathogen that induces northern leaf blight infection. The fungal pathogen is also referred to herein as *Exserohilum* or Et.

"Disease resistance" (such as, for example, northern leaf blight resistance) is a characteristic of a plant, wherein the plant avoids the disease symptoms that are the outcome of plant-pathogen interactions, such as maize-*Exserohilum turcicum* interactions. That is, pathogens are prevented from causing plant diseases and the associated disease symptoms, or alternatively, the disease symptoms caused by the pathogen are minimized or lessened. One of skill in the art will appreciate that the compositions and methods disclosed herein can be used with other compositions and methods available in the art for protecting plants from pathogen attack.

"Resistance" is a relative term, indicating that the infected plant produces better yield of maize than another, similarly treated, more susceptible plant. That is, the conditions cause a reduced decrease in maize survival and/or yield in a tolerant maize plant, as compared to a susceptible maize plant. One of skill will appreciate that maize plant resistance to northern leaf blight, or the pathogen causing such, can represent a spectrum of more resistant or less resistant phenotypes, and can vary depending on the severity of the infection. However, by simple observation, one of skill can determine the relative resistance or susceptibility of different plants, plant lines or plant families to northern leaf blight, and furthermore, will also recognize the phenotypic gradations of "resistant". For example, a 1 to 9 visual rating indicating the level of resistance to northern leaf blight can be used. A higher score indicates a higher resistance. Data should be collected only when sufficient selection pressure exists in the experiment measured. The terms "tolerance" and "resistance" are used interchangeably herein.

The resistance may be "newly conferred" or "enhanced". "Newly conferred" or "enhanced" resistance refers to an increased level of resistance against a particular pathogen, a wide spectrum of pathogens, or an infection caused by the pathogen(s). An increased level of resistance against a particular fungal pathogen, such as Et, for example, constitutes "enhanced" or improved fungal resistance. The embodiments of the invention will enhance or improve fungal plant pathogen resistance, such that the resistance of the plant to a fungal pathogen or pathogens will increase, which in turn, will increase resistance to the disease caused by the fungal pathogen. The term "enhance" refers to improve, increase, amplify, multiply, elevate, raise, and the like.

The maize plants generated by the methods described herein may provide durable and broad spectrum resistance to the maize plant and may assist in breeding of northern leaf blight resistant maize plants. For instance, if multiple northern leaf blight resistance genes are stacked into one unit, this reduces the number of specific loci that require trait introgression through backcrossing and minimizes linkage drag from non-elite resistant donors.

Various methods can be used to introduce a sequence of interest into a maize plant cell, maize plant or maize plant part. "Introducing" is intended to mean presenting to the maize plant cell, maize plant, or maize plant part the polynucleotide in such a manner that the sequence gains access to the interior of a cell of the maize plant. The methods of the disclosure do not depend on a particular method for introducing a sequence into an organism or a maize plant or maize plant part, only that the polynucleotide gains access to the interior of at least one cell of the maize plant. Methods for introducing polynucleotides into various organisms, including maize plants, are known in the art, including, but not limited to, stable transformation methods, transient transformation methods, and virus-mediated methods.

"Stable transformation" is intended to mean that the polynucleotide construct introduced into a maize plant integrates into the genome of the maize plant and is capable of being inherited by the progeny thereof. "Transient transformation" is intended to mean that a polynucleotide is introduced into the maize plant and does not integrate into the genome of the maize plant.

Transformation protocols as well as protocols for introducing polynucleotide sequences into plants such as maize may vary. Suitable methods of introducing polynucleotides into maize plant cells include microinjection (Crossway et al. (1986) *Biotechniques* 4:320 334), electroporation (Riggs et al. (1986) *Proc. Natl. Acad. Sci. USA* 83:5602 5606, *Agrobacterium*-mediated transformation (U.S. Pat. Nos. 5,563,055 and 5,981,840), direct gene transfer (Paszkowski et al. (1984) *EMBO J.* 3:2717 2722), and ballistic particle acceleration (see, for example, U.S. Pat. Nos. 4,945,050; 5,879,918; 5,886,244; and, 5,932,782; Tomes et al. (1995) in

*Plant Cell, Tissue, and Organ Culture: Fundamental Methods*, ed. Gamborg and Phillips (Springer-Verlag, Berlin); McCabe et al. (1988) *Biotechnology* 6:923 926); and Lec1 transformation (WO 00/28058). Also see Klein et al. (1988) *Proc. Natl. Acad. Sci. USA* 85:4305 4309 (maize); Klein et al. (1988) *Biotechnology* 6:559 563 (maize); U.S. Pat. Nos. 5,240,855; 5,322,783; and, 5,324,646; Klein et al. (1988) *Plant Physiol.* 91:440 444 (maize); Fromm et al. (1990) *Biotechnology* 8:833 839 (maize); Hooykaas-Van Slogteren et al. (1984) *Nature* (London) 311:763-764; U.S. Pat. No. 5,736,369 (cereals); De Wet et al. (1985) in *The Experimental Manipulation of Ovule Tissues*, ed. Chapman et al. (Longman, New York), pp. 197-209 (pollen); D'Halluin et al. (1992) *Plant Cell* 4:1495-1505 (electroporation); and Osjoda et al. (1996) *Nature Biotechnology* 14:745-750 (maize via *Agrobacterium tumefaciens*); all of which are herein incorporated by reference.

In other embodiments, the Ht1 polynucleotide disclosed herein thereof may be introduced into plants by contacting plants with a virus or viral nucleic acids. Generally, such methods involve incorporating a polynucleotide construct of the disclosure within a DNA or RNA molecule. It is recognized that the Ht1 sequence may be initially synthesized as part of a viral polyprotein, which later may be processed by proteolysis in vivo or in vitro to produce the desired recombinant protein. Further, it is recognized that promoters disclosed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide disclosed herein can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome. Other methods to target polynucleotides are set forth in WO 2009/114321 (herein incorporated by reference), which describes "custom" meganucleases produced to modify plant genomes, in particular the genome of maize. See, also, Gao et al. (2010) *Plant Journal* 1:176-187.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a polynucleotide disclosed herein, for example, as part of an expression cassette, stably incorporated into their genome.

Transformed maize plant cells which are derived by plant transformation techniques, including those discussed above, can be cultured to regenerate a whole plant which possesses the transformed genotype (i.e., an Ht1 polynucleotide that encodes a polypeptide that confers resistance to northern leaf blight), and thus the desired phenotype, such as resistance to northern leaf blight, whether that resistance is newly conferred or enhanced. For transformation and regeneration of maize see, Gordon-Kamm et al., *The Plant Cell,* 2:603-618 (1990). Plant regeneration from cultured protoplasts is described in Evans et al. (1983) Protoplasts Isolation and Culture, Handbook of Plant Cell Culture, pp 124-176, Macmillan Publishing Company, New York; and Binding (1985) Regeneration of Plants, Plant Protoplasts pp 21-73, CRC Press, Boca Raton. Regeneration can also be obtained from plant callus, explants, organs, or parts thereof. Such regeneration techniques are described generally in Klee et al. (1987) *Ann Rev of Plant Phys* 38:467. See also, e.g., Payne and Gamborg.

One of skill will recognize that after the expression cassette containing the Ht1 gene is stably incorporated in transgenic plants and confirmed to be operable, it can be introduced into other plants by sexual crossing. Any of a number of standard breeding techniques can be used, depending upon the species to be crossed.

In some embodiments, the methods comprise introducing by way of expressing in a regenerable maize plant cell a polynucleotide construct comprising a polynucleotide operably linked to at least one regulatory sequence, wherein the polynucleotide encodes a resistant allele of the Ht1 gene presented herein, and generating a maize plant that has resistance to northern leaf blight from the maize plant cell. The maize plant generated by the method comprises in its genome the polynucleotide construct. The regulatory sequence may be a promoter and/or a terminator and may be native to maize. In some embodiments, the regulatory sequence is native to the Ht1 gene. A progeny plant comprising the polynucleotide construct may also be generated by crossing the maize plant generated by the method to a second maize plant that does not comprise in its genome the polynucleotide construct. In some embodiments, the Ht1 gene is overexpressed (either as a genomic fragment or cDNA) to impart greater resistance than the level of expression in the native state.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1

Fine Mapping of Northern Leaf Blight Resistance Locus

A large backcross-derived population was created for fine mapping of a northern leaf blight resistance QTL located on chromosome 2. The population was created from a cross between resistant line PH4GP (score=9) and susceptible line PH5W4 (score=1), and the susceptible line was used as the recurrent parent. BC5 individuals were scored for northern leaf blight infection using the phenotyping method disclosed in U.S. Pat. No. 8,921,646. Marker recombination data from a large set of individuals from population 2 placed the gene in an 18 kb region in the B73 genome, encompassing a putative protein phosphatase 2C, a putative PHD-type zinc finger protein, and a putative disease resistance protein. There is no known EST for the putative disease resistance protein; moreover, based on the B73 predicted gene sequence, the putative disease resistance protein has low, constitutive expression.

Example 2

Identification of Candidate Gene for Ht1 and Comparison of Allelic Variants

A BAC library from resistant donor PH4GP was constructed, and a BAC clone covering the Ht1 interval was identified and sequenced. The Ht1 interval in PH4GP was less than 10 kb, with only a single annotated gene that encodes a putative CC-NB-LRR (coiled-coil, nucleotide-binding, leucine-rich repeat) gene. Ht1 cDNA sequences from PH4GP and from PH1W2 (another source of a resistant allele of Ht1; US2010095395) are represented by SEQ ID NOs:1 and 3, respectively, while the amino acid sequences of the encoded polypeptides are represented by SEQ ID NO:2 and 4. B73 has two splicing variants, and the novel variant expresses at a much higher level (referred to herein as B73-high) than the known variant (referred to herein as B73-low). SEQ ID NO:5 is the cDNA sequence of the B73-high allele, while the amino acid sequence of the encoded polypeptide is represented by SEQ ID NO:6. SEQ ID NO:7 is the cDNA sequence of the B73-low allele, while the amino acid sequence of the encoded polypeptide is represented by SEQ ID NO:8.

FIGS. 1A-1D show that the CC and NB domains are highly similar between the susceptible allele (from B73) and resistant alleles (from PH4GP and PH1W2). However, both B73 alleles have a deletion in the LRR (shown boxed in FIG. 1C). The amino acid sequence of this region in the Ht1 resistant alleles is represented by SEQ ID NO:10.

Example 3

Transgenic Validation

A construct containing the genomic sequence of the PH4GP (resistant) allele (SEQ ID NO:9) was generated and transformed into a susceptible transformation line using *Agrobacterium*-mediated transformation. The genomic sequence (SEQ ID NO:9) contained the native promoter, exons, intron and terminator regions. Regenerated transgenic plants were planted in a greenhouse, and a quantitative PCR analysis was done to confirm insertion of the T-DNA cassette that contains the genomic sequence of the PH4GP (resistant) allele. Many of the events had a single copy of the T-DNA insert, which was confirmed by qPCR using four flanking markers. Based on the marker data, of the 50 events, 41 were positive for the insert and 9 were negative (null).

All events were tested in the greenhouse for efficacy against the northern leaf blight pathogen (*Exserohilum turcicum*). First, all events were challenged with race 0 of the pathogen for which Ht1 gene is known to provide resistance; then the events were subjected to race 1, to which Ht1 does not provide resistance. All positive events, as determined by qPCR, were resistant to race 0, and all negative events were susceptible to race 0. As expected, all events were susceptible to race 1.

Example 4

Production of Northern Leaf Blight Resistant Maize Plants Expressing the Maize Ht1 Polypeptide Northern leaf blight resistant maize plants expressing the maize Ht1 gene can be produced using recombinant DNA-based transformation, for example. Recombinant DNA based transformation methods are well known in the art, e.g. *Agrobacterium tumefaciens*-mediated and particle bombardment based transformations. With respect to *Agrobacterium tumefaciens* based plant transformation, vectors are constructed according to methods known in the art. The vectors contain a T-DNA insert having a promoter, an intron, an optional enhancer such as a 35S enhancer element, an Ht1 variant DNA that confers resistance to northern leaf blight, and a plant terminator. Maize immature embryos are excised and infected with an *Agrobacterium tumefaciens* vector containing the Ht1 variant of interest. After infection, embryos are transferred and cultured in co-cultivation medium. After co-cultivation, the infected immature embryos are transferred onto media to grow transgenic calli. The putative transgenic callus tissues are sampled using PCR and optionally a Western assay to confirm the presence of the Ht1 variant gene. The putative transgenic callus tissues are maintained on media for further growth and selection before plant regeneration. At regeneration, callus tissue confirmed to be transgenic are transferred onto maturation medium and cultured for somatic embryo maturation. Mature embryos are then transferred onto regeneration medium for shoot and root formation. After shoots and roots emerge, individual plantlets are transferred into tubes with rooting medium. Plantlets with established shoots and roots are transplanted into pots in the greenhouse for further growth and to produce T1 seed.

Furthermore, a DNA construct containing an Ht1 variant DNA that confers resistance to northern leaf blight may also include another gene encoding a polypeptide that confers northern leaf blight resistance, such as the gene encoding for NLB18 (in WO2011163590). Both PH99N and PH26N are maize lines showing resistance to northern leaf blight that reflect different sources of resistance with respect to the chromosome 8 QTL, as described in application WO2011163590. The amino acid sequence of the NLB18 polypeptide from line PH99N is presented herein as SEQ ID NO:11; the amino acid sequence of the NLB18 polypeptide from line PH26N is presented herein as SEQ ID NO:12. The introduction of Ht1 and NLB18 in a plant may have the effect of increasing resistance to race 0 of the *Exserohilum turcicum* pathogen and/or may provide resistance to an additional race or races (e.g. race 1), for which the Ht1 gene does not provide resistance.

What is claimed is:

1. A maize plant cell comprising a heterologous polynucleotide construct comprising an isolated polynucleotide operably linked to a regulatory element, wherein the isolated polynucleotide comprises:
   a. the nucleotide sequence set forth in SEQ ID NO:1 (PH4GP c-DNA), SEQ ID NO:3 (PH1W2 cDNA), or SEQ ID NO:9 (PH4GP Genomic sequence);
   b. a nucleotide sequence encoding a CC-NB-LRR polypeptide comprising an amino acid sequence of at least 95% sequence identity to SEQ ID NO:2 or SEQ ID NO:4, wherein the CC-NB-LRR polypeptide comprises SEQ ID NO:10 at the positions corresponding to amino acids 633-648 of SEQ ID NO:2 or SEQID NO:4, respectively; or
   c. a nucleotide sequence encoding a CC-NB-LRR polypeptide comprising the sequence set forth in SEQ ID NO:2 or SEQ ID NO:4.

2. The maize plant cell of claim 1, wherein the polynucleotide construct further comprises one or more additional heterologous nucleic acid sequences that encode a polypeptide selected from the group consisting of: a polypeptide conferring disease resistance, a polypeptide conferring herbicide resistance, a polypeptide conferring insect resistance, a polypeptide involved in carbohydrate metabolism, a polypeptide involved in fatty acid metabolism, a polypeptide involved in amino acid metabolism, a polypeptide involved in plant development, a polypeptide involved in plant growth regulation, a polypeptide involved in yield improvement, a polypeptide involved in drought resistance, a polypeptide involved in cold resistance, a polypeptide involved in heat resistance, and/or a polypeptide involved in salt resistance, wherein each heterologous nucleic acid sequence is operably linked to a promoter.

3. The maize plant cell of claim 2, wherein a polypeptide conferring disease resistance is a polypeptide that confers resistance to northern leaf blight (NLB).

4. The maize plant cell of claim 3, wherein said polypeptide conferring resistance to northern leaf blight is a polypeptide having an amino acid sequence of at least 90% sequence identity when compared to SEQ ID NO:11 or 12.

5. A maize plant comprising the maize plant cell of claim 1.

6. A method for producing a maize plant that exhibits increased resistance to northern leaf blight (NLB) comprising,
expressing in the plant a heterologous polynucleotide construct comprising a polynucleotide operably linked to at least one regulatory sequence, wherein the polynucleotide comprises:
  i. a nucleotide sequence set forth in SEQ ID NO:1 (PH4GP c-DNA), SEQ ID NO:3 (PH1W2 cDNA), or SEQ ID NO:9 (PH4GP Genomic sequence);
  ii. a nucleotide sequence encoding a CC-NB-LRR polypeptide comprising an amino acid sequence of at least 95% sequence identity when compared to SEQ ID NO:2 or SEQ ID NO:4, wherein said polypeptide comprises the amino acid sequence set forth in SEQ ID NO:10;
  iii. a nucleotide sequence encoding a CC-NB-LRR polypeptide having the sequence set forth in SEQ ID NO:2 or SEQ ID NO:4; or
  iv. the nucleotide sequence complementary to (i), (ii), or (iii); and thereby generating a maize plant that exhibits increased resistance to northern leaf blight, wherein said maize plant comprises in its genome the heterologous polynucleotide construct.

7. The method of claim 6, wherein said at least one regulatory sequence is a promoter.

8. The method of claim 6, wherein said at least one regulatory sequence is a terminator.

9. The method of claim 6, wherein said regulatory sequence is native to maize.

10. The method of claim 6, wherein said polynucleotide construct comprises one or more additional heterologous nucleic acid sequences that encode a polypeptide selected from the group consisting of: a polypeptide conferring disease resistance, a polypeptide conferring herbicide resistance, a polypeptide conferring insect resistance, a polypeptide involved in carbohydrate metabolism, a polypeptide involved in fatty acid metabolism, a polypeptide involved in amino acid metabolism, a polypeptide involved in plant development, a polypeptide involved in plant growth regulation, a polypeptide involved in yield improvement, a polypeptide involved in drought resistance, a polypeptide involved in cold resistance, a polypeptide involved in heat resistance, and/or a polypeptide involved in salt resistance, wherein each heterologous nucleic acid sequence is operably linked to a promoter.

11. The method of claim 10, wherein the polypeptide conferring disease resistance is a polypeptide that confers resistance to northern leaf blight (NLB).

12. The method of claim 11, wherein said polypeptide conferring resistance to northern leaf blight is a polypeptide having an amino acid sequence of at least 90% sequence identity when compared to SEQ ID NO:11 or 12.

13. A method of obtaining a maize plant that exhibits resistance to northern leaf blight (NLB), said method comprising,
  a. crossing a maize plant generated by the method of claim 6 with a maize plant that does not comprise in its genome the polynucleotide construct;
  b. obtaining a progeny plant that exhibits resistance to northern leaf blight, wherein said progeny plant comprises the polynucleotide construct in its genome.

14. The maize plant cell of claim 1, wherein the isolated polynucleotide comprises a nucleotide sequence encoding a CC-NB-LRR polypeptide comprising an amino acid sequence of at least 95% sequence identity to SEQ ID NO:2 or SEQ ID NO:4, wherein the CC-NB-LRR polypeptide comprises SEQ ID NO:10 at the positions corresponding to amino acids 633-648 of SEQ ID NO:2 or SEQID NO:4, respectively.

15. The maize plant cell of claim 1, wherein the isolated polynucleotide comprises a nucleotide sequence encoding a CC-NB-LRR polypeptide comprising the sequence set forth in SEQ ID NO:2 or SEQ ID NO:4.

16. The method of claim 6, wherein the polynucleotide operably linked to at least one regulatory sequence comprises a nucleotide sequence encoding a CC-NB-LRR polypeptide comprising an amino acid sequence of at least 95% sequence identity when compared to SEQ ID NO:2 or SEQ ID NO:4, wherein said polypeptide comprises the amino acid sequence set forth in SEQ ID NO:10.

17. The method of claim 6, wherein the polynucleotide operably linked to at least one regulatory sequence comprises a nucleotide sequence encoding a CC-NB-LRR polypeptide having the sequence set forth in SEQ ID NO:2 or SEQ ID NO:4.

18. The maize plant cell of claim 1, wherein the isolated polynucleotide comprises the nucleotide sequence set forth in SEQ ID NO:9.

19. The method of claim 6, wherein the polynucleotide operably linked to at least one regulatory sequence comprises the nucleotide sequence set forth in SEQ ID NO:9.

* * * * *

SEQUENCE LISTING

<160> NUMBER OF SEQ ID NOS: 12

<210> SEQ ID NO 1
<211> LENGTH: 2658
<212> TYPE: DNA
<213> ORGANISM: Zea mays

<400> SEQUENCE: 1

| | | | | | |
|---|---|---|---|---|---|
| atggagaacc | cagacgcgca | ggcgaaggcg | tgggcggcgg | agatgcgcga | gctggcctac | 60 |
| gacatggagg | acagcatcga | tctcttcacc | caccacgtcg | accacgaacc | ggccgacacc | 120 |
| gccaccaccg | gcgtcaagag | gttcttcctc | cggatcatcc | ggaagcttaa | gaaactccac | 180 |
| taccgccaca | ggtttgttca | ggagatcaaa | caactccacg | accttgccaa | cgaatcgtac | 240 |
| cggcgtagga | agaggtacag | gattgaggag | ggcggttcaa | gcctctcgca | cgcggagatc | 300 |
| gatcctcggt | tagaggcgct | ctacgtggag | gtggagaaac | tcgtgggcat | ccagggccca | 360 |
| agccaggaga | tcattggaca | gctcgtcggc | gagaacgcag | cggagcgacg | gagggttgtc | 420 |
| gccgttgttg | gatctggagg | ttcaggcaag | accacacttg | ccaaacaggt | gtacgagaaa | 480 |
| atcaggtgcc | aattctcttg | tgcagccttt | gtgtctgtgt | cgcaaaagcc | caacatgaat | 540 |
| agcctcctgt | gggagttgct | atctcaaatc | gggaaccatg | gtggagattt | aggaatgatg | 600 |
| gcagtaggat | attgcagtga | caaacaactg | atcgacagac | taagatcaca | tcttgaaaag | 660 |
| cagaggtatc | tcgttgtgat | agatgatgtt | tggacaaact | cagcgtggga | gaccatacaa | 720 |
| tgtgcgctcc | ctaaaaatgc | ccatgcaagt | aaaataattc | tgacaacacg | aatcaacagt | 780 |
| gtaggccagt | tctcctgcac | tccagatgag | ggttttatct | atcagatgaa | gcctcttttgc | 840 |
| agaaacgatt | ctgaaaatct | gtttctgaaa | ggacactat | gtgataaaga | taagtttcct | 900 |
| gctcagctgg | aggggattaa | aaacgagata | tcgagaaat | gcgatggttt | gccactggct | 960 |
| attgttactc | tagctagcat | gttagctact | aaacagagaa | caaggaaga | atgggagagg | 1020 |
| gcacttgatt | caatccattc | tatgcacaag | aaagatagtg | gcctggaagt | gatggacaag | 1080 |
| atactgtctc | tgagttacag | ggatctacct | cacaacatga | aaattgctt | gctgtatctc | 1140 |
| agtacatttc | cagaggacca | cacgatttac | aaagatgccc | tagtatggag | atggatggct | 1200 |
| gaagggttta | tcgctgaaac | acaaggcttt | actttggagc | aggttgccga | gggctacttc | 1260 |
| tacgagtttg | tgaacaggag | tttggttcag | cccataacct | tgcgttcaag | atatgaaatg | 1320 |
| cgtggagaag | gaggttgccg | agtccatgac | attgtactga | acttcctcat | ctctcgtgca | 1380 |
| gctgaagaga | acttttttaac | tacgctgtat | ggcgcccagg | gggttccatc | ttcagaccga | 1440 |
| aggattcgcc | ggctctctgt | ctgggacagt | ccagaacacg | cactggcagt | ctctagagcg | 1500 |
| accatgaatc | tgtcccatct | ccggtcagtt | agaatatgca | acgttggaga | ctggcccgtg | 1560 |
| cctgctgttc | tagacttacc | tgtccttcga | gtgttagatc | tagagggatg | ccgtgatctg | 1620 |
| aggatcgacg | aacctgactg | cattctaagc | ttgtttcatc | tgagatacct | gggtttccgc | 1680 |
| agcgcaagtg | gtgtcgtgct | accggctcaa | atcggaaatt | tacaccatct | gcagaccatc | 1740 |
| gatttaagcg | ggactggagt | gacacagctg | ccagaaagca | ttgtccagct | caagcgactg | 1800 |
| atgcatcttg | ttgggcaacg | gctcatcatg | ccagacgggt | tggtagcat | ggaatccctt | 1860 |
| gaggagttag | gtactatcga | ctgctgcaag | tgccccgtca | gttttgggga | agacctagca | 1920 |
| cttctgagca | ggctgagggt | gctccgagtg | gctttcatcg | gggtcgaaac | aagtgacatg | 1980 |
| gaaaccagaa | ggaaatcttt | gatgtcatcc | ctctgcaaac | tcgaggagaa | caaccttcgg | 2040 |
| cgtgtcacta | ttatcgaccc | tgctggcggt | ggagattgct | ttgtggagtc | gtggcaccct | 2100 |

-continued

```
cctcctcgtc tcctccagaa gttcatccat atcagtcagc aacagcactt ctccaggttt     2160
ccagaatgga tcagttcctg cctatgtgat ctcacccacc tggatataaa ggccgaaaag     2220
atggaaaggg agcatctaag tgttcttgaa cacctgcccg ccatccgttg cctatacctt     2280
ttcgtgaagc gagtctccga agacgggctc gccatcagcc acggcgcgtt ccgatgtcta     2340
cggcgtctcg agttctgcaa cgtagatgga cctggtttga tgtttgcagg aggcgttcca     2400
atgttggaat ggctgaggct cgggttcgac gcggatagag cgcaatcgac atacggcggt     2460
ctggaggttg gcatccagcg cctctcgtct ctcaaacatg tcgtgctcat tgtatggatg     2520
gtttctgaag gcggtgatga tccagcgagc aagccgtct ggtctgccat caatggccaa     2580
gtagagatgc tccccaactc tccgacggtt gatatccggt ttcgtagacg gagtcagctg     2640
caggcaagct cagaataa                                                   2658
```

<210> SEQ ID NO 2
<211> LENGTH: 885
<212> TYPE: PRT
<213> ORGANISM: Zea mays

<400> SEQUENCE: 2

```
Met Glu Asn Pro Asp Ala Gln Ala Lys Ala Trp Ala Ala Glu Met Arg
1               5                   10                  15

Glu Leu Ala Tyr Asp Met Glu Asp Ser Ile Asp Leu Phe Thr His His
            20                  25                  30

Val Asp His Glu Pro Ala Asp Thr Ala Thr Thr Gly Val Lys Arg Phe
        35                  40                  45

Phe Leu Arg Ile Ile Arg Lys Leu Lys Lys Leu His Tyr Arg His Arg
    50                  55                  60

Phe Val Gln Glu Ile Lys Gln Leu His Asp Leu Ala Asn Glu Ser Tyr
65                  70                  75                  80

Arg Arg Arg Lys Arg Tyr Arg Ile Glu Glu Gly Gly Ser Ser Leu Ser
                85                  90                  95

His Ala Glu Ile Asp Pro Arg Leu Glu Ala Leu Tyr Val Glu Val Glu
            100                 105                 110

Lys Leu Val Gly Ile Gln Gly Pro Ser Gln Glu Ile Ile Gly Gln Leu
        115                 120                 125

Val Gly Glu Asn Ala Ala Glu Arg Arg Val Val Ala Val Val Gly
    130                 135                 140

Ser Gly Gly Ser Gly Lys Thr Thr Leu Ala Lys Gln Val Tyr Glu Lys
145                 150                 155                 160

Ile Arg Cys Gln Phe Ser Cys Ala Ala Phe Val Ser Val Ser Gln Lys
                165                 170                 175

Pro Asn Met Asn Ser Leu Leu Trp Glu Leu Leu Ser Gln Ile Gly Asn
            180                 185                 190

His Gly Gly Asp Leu Gly Met Met Ala Val Gly Tyr Cys Ser Asp Lys
        195                 200                 205

Gln Leu Ile Asp Arg Leu Arg Ser His Leu Glu Lys Gln Arg Tyr Leu
    210                 215                 220

Val Val Ile Asp Asp Val Trp Thr Asn Ser Ala Trp Glu Thr Ile Gln
225                 230                 235                 240

Cys Ala Leu Pro Lys Asn Ala His Ala Ser Lys Ile Ile Leu Thr Thr
                245                 250                 255

Arg Ile Asn Ser Val Gly Gln Phe Ser Cys Thr Pro Asp Glu Gly Phe
            260                 265                 270
```

```
Ile Tyr Gln Met Lys Pro Leu Cys Arg Asn Asp Ser Glu Asn Leu Phe
        275                 280                 285

Leu Lys Arg Thr Leu Cys Asp Lys Asp Lys Phe Pro Ala Gln Leu Glu
        290                 295                 300

Gly Ile Lys Asn Glu Ile Ile Glu Lys Cys Asp Gly Leu Pro Leu Ala
305                 310                 315                 320

Ile Val Thr Leu Ala Ser Met Leu Ala Thr Lys Gln Arg Thr Arg Glu
                    325                 330                 335

Glu Trp Glu Arg Ala Leu Asp Ser Ile His Ser Met His Lys Lys Asp
                340                 345                 350

Ser Gly Leu Glu Val Met Asp Lys Ile Leu Ser Leu Ser Tyr Arg Asp
            355                 360                 365

Leu Pro His Asn Met Arg Asn Cys Leu Leu Tyr Leu Ser Thr Phe Pro
        370                 375                 380

Glu Asp His Thr Ile Tyr Lys Asp Ala Leu Val Trp Arg Trp Met Ala
385                 390                 395                 400

Glu Gly Phe Ile Ala Glu Thr Gln Gly Phe Thr Leu Glu Gln Val Ala
                    405                 410                 415

Glu Gly Tyr Phe Tyr Glu Phe Val Asn Arg Ser Leu Val Gln Pro Ile
                420                 425                 430

Thr Leu Arg Ser Arg Tyr Glu Met Arg Gly Glu Gly Cys Arg Val
            435                 440                 445

His Asp Ile Val Leu Asn Phe Leu Ile Ser Arg Ala Ala Glu Glu Asn
        450                 455                 460

Phe Leu Thr Thr Leu Tyr Gly Ala Gln Gly Val Pro Ser Ser Asp Arg
465                 470                 475                 480

Arg Ile Arg Arg Leu Ser Val Trp Asp Ser Pro Glu His Ala Leu Ala
                    485                 490                 495

Val Ser Arg Ala Thr Met Asn Leu Ser His Leu Arg Ser Val Arg Ile
                500                 505                 510

Cys Asn Val Gly Asp Trp Pro Val Pro Ala Val Leu Asp Leu Pro Val
            515                 520                 525

Leu Arg Val Leu Asp Leu Glu Gly Cys Arg Asp Leu Arg Ile Asp Glu
        530                 535                 540

Pro Asp Cys Ile Leu Ser Leu Phe His Leu Arg Tyr Leu Gly Phe Arg
545                 550                 555                 560

Ser Ala Ser Gly Val Val Leu Pro Ala Gln Ile Gly Asn Leu His His
                    565                 570                 575

Leu Gln Thr Ile Asp Leu Ser Gly Thr Gly Val Thr Gln Leu Pro Glu
                580                 585                 590

Ser Ile Val Gln Leu Lys Arg Leu Met His Leu Val Gly Gln Arg Leu
            595                 600                 605

Ile Met Pro Asp Gly Phe Gly Ser Met Glu Ser Leu Glu Glu Leu Gly
        610                 615                 620

Thr Ile Asp Cys Cys Lys Cys Pro Val Ser Phe Gly Glu Asp Leu Ala
625                 630                 635                 640

Leu Leu Ser Arg Leu Arg Val Leu Arg Val Ala Phe Ile Gly Val Glu
                    645                 650                 655

Thr Ser Asp Met Glu Thr Arg Arg Lys Ser Leu Met Ser Ser Leu Cys
                660                 665                 670

Lys Leu Gly Gly Asp Asn Leu Arg Arg Val Thr Ile Ile Asp Leu Ala
            675                 680                 685
```

```
Gly Gly Gly Asp Cys Phe Val Glu Ser Trp His Pro Pro Arg Leu
    690                 695                 700
Leu Gln Lys Phe Ile His Ile Ser Gln Gln His Phe Ser Arg Phe
705                 710                 715                 720
Pro Glu Trp Ile Ser Ser Cys Leu Cys Asp Leu Thr His Leu Asp Ile
                725                 730                 735
Lys Ala Glu Lys Met Glu Arg Glu His Leu Ser Val Leu Glu His Leu
                740                 745                 750
Pro Ala Ile Arg Cys Leu Tyr Leu Phe Val Lys Arg Val Ser Glu Asp
                755                 760                 765
Gly Leu Ala Ile Ser His Gly Ala Phe Arg Cys Leu Arg Arg Leu Glu
    770                 775                 780
Phe Cys Asn Val Asp Gly Pro Gly Leu Met Phe Ala Gly Gly Val Pro
785                 790                 795                 800
Met Leu Glu Trp Leu Arg Leu Gly Phe Asp Ala Asp Arg Ala Gln Ser
                805                 810                 815
Thr Tyr Gly Gly Leu Glu Val Gly Ile Gln Arg Leu Ser Ser Leu Lys
    820                 825                 830
His Val Val Leu Ile Val Trp Met Val Ser Glu Gly Gly Asp Asp Pro
    835                 840                 845
Ala Glu Gln Ala Val Trp Ser Ala Ile Asn Gly Gln Val Glu Met Leu
    850                 855                 860
Pro Asn Ser Pro Thr Val Asp Ile Arg Phe Arg Arg Ser Gln Leu
865                 870                 875                 880
Gln Ala Ser Ser Glu
```

<210> SEQ ID NO 3
<211> LENGTH: 2652
<212> TYPE: DNA
<213> ORGANISM: Zea mays

<400> SEQUENCE: 3

```
atggagaacc cagacgcgca ggcgaaggcg tgggcggcgg agatgcgcga gctggcctac      60
gacatggagg acagcatcga tctcttcacc caccacgtcg accacgaacc ggccgacacc     120
gccaccaccg gcgtcaagag gttcttcctc cggatcatcc ggaagcttaa gaaactccac     180
taccgccaca ggtttgttca ggagatcaaa caactccacg accttgccaa cgaatcgtac     240
cggcgtagga agaggtacag gattgaggag gcgggttcaa gcctctcgca cgcggagatc     300
gatcctcggt tagaggcgct ctacgtggag gtggagaaac tcgtgggcat ccagggccca     360
agccaggaga tcattggaca gctcgtcggc gagaacgcag cggagcgacg gagggttgtc     420
gccgttgttg gatctggagg ttcaggcaag accacacttg ccaaacaggt gtacgagaaa     480
atcaggtgcc aattctcttg tgcagccttt gtgtctgtgt cgcaaaagcc aacatgaat      540
agcctcctgt gggagttgct atctcaaatc gggaaccatg gtggagattt aggaatgatg     600
gcagtaggat attgcagtga caaacaactg atcgacagac taagatcaca tcttgaaaag     660
cagaggtatc tcgttgtgat agatgatgtt tggacaaact cagcgtggga gaccatacaa     720
tgtgcgctcc ctaaaaatgc ccatgcaagt aaaataattc tgacaacacg aatcaacagt     780
gtaggccagt tctcctgcac tccagatgag ggttttatct atcagatgaa gcctctttgc     840
agaaacgatt ctgaaaatct gtttctgaaa aggacactat gtgataaaga taagtttcct     900
gctcagctgg aggggattaa aaacgagata tcgagaaat gcgatggttt gccactggct     960
attgttactc tagctagcat gttagctact aaacagagaa caagggaaga atgggagagg    1020
```

```
gcacttgatt caatccattc tatgcacaag aaagatagtg gcctggaagt gatggacaag    1080
atactgtctc tgagttacag ggatctacct cacaacatga gaaattgctt gctgtatctc    1140
agtacatttc cagaggacca cacgatttac aaagatgccc tagtatggag atggatggct    1200
gaagggttta tcgctgaaac acaaggcttt actttggagc aggttgccga gggctacttc    1260
tacgagtttg tgaacaggag tttggttcag cccataacct tgcgttcaag atatgaaatg    1320
cgtggagaag gaggttgccg agtccatgac attgtactga acttcctcat ctctcgtgca    1380
gctgaagaga acttttttaac tacgctgtat ggcgcccagg gggttccatc ttcagaccga    1440
aggattcgcc ggctctctgt ctgggacagt ccagaacacg cactggcagt ctctagagcg    1500
accatgaatc tgtcccatct ccggtcagtt agaatatgca acgttggaga ctggcccgtg    1560
cctgctgttc tagacttacc tgtccttcga gtgttagatc tagagggatg ccgtgatctg    1620
aggatcgacg aacctgactg cattctaagc ttgtttcatc tgagatacct gggtttccgc    1680
agcgcaagtg gtgtcgtgct accggctcaa atcggaaatt tacaccatct gcagaccatc    1740
gatttaagcg ggactggagt gacacagctg ccagaaagca ttgtccagct caagcgactg    1800
atgcatcttg ttgggcaacg gctcatcatg ccagacgggt ttggtagcat ggaatccctt    1860
gaggagttag gtactatcga ctgctgcaag tgccccgtca gttttgggga agacctagca    1920
cttctgagca ggctgagggt gctccgagtg gctttcatcg gggtcgaaac aagtgacatg    1980
gaaaccagaa ggaaatcttt gatgtcatcc ctctgcaaac tcggaggaga caaccttcgg    2040
cgtgtcacta ttatcgacct cgctggcggt ggagattgct tgtgtgagtc gtggcaccct    2100
cctcctcgtc tcctccagaa gttcatccat atcagtcagc acttctccag gtttccagaa    2160
tggatcagtt cctgcctatg tgatctcacc cacctggata taaaggccga aaagatggaa    2220
agggagcatc taagtgttct tgaacacctg cccgccatcc gttgcctata ccttttcgtg    2280
aagcgagtct ccgaagacgg gctcgtcatc agccacggcg cgttccgatg tctacggcgt    2340
ctcgagttct gtaacgtaga tggacctggt ttgatgtttg caggaggcgt tccaatgttg    2400
gaatggctga ggctcgggtt cgacgcggat agagcgcaat cgacatacgg cggtctggag    2460
gttggcatcc agcgcctctc gtctctcaaa catgtcgtgc tcattgtatg gatggttct     2520 gaaggcggtg atgatccagc ggagcaagcc gtctggtctg ccatcaatgg ccaagtagag    2580
atgctcccca actctccgac ggttgatatc cggtttcgta gacggagtca gctgcaggca    2640
agctcagaat aa                                                        2652
```

<210> SEQ ID NO 4
<211> LENGTH: 883
<212> TYPE: PRT
<213> ORGANISM: Zea mays

<400> SEQUENCE: 4

Met Glu Asn Pro Asp Ala Gln Ala Lys Ala Trp Ala Ala Glu Met Arg
1               5                   10                  15

Glu Leu Ala Tyr Asp Met Glu Asp Ser Ile Asp Leu Phe Thr His His
            20                  25                  30

Val Asp His Glu Pro Ala Asp Thr Ala Thr Thr Gly Val Lys Arg Phe
        35                  40                  45

Phe Leu Arg Ile Ile Arg Lys Leu Lys Lys Leu His Tyr Arg His Arg
    50                  55                  60

Phe Val Gln Glu Ile Lys Gln Leu His Asp Leu Ala Asn Glu Ser Tyr
65                  70                  75                  80

```
Arg Arg Arg Lys Arg Tyr Arg Ile Glu Glu Gly Gly Ser Ser Leu Ser
                85                  90                  95

His Ala Glu Ile Asp Pro Arg Leu Glu Ala Leu Tyr Val Glu Val Glu
            100                 105                 110

Lys Leu Val Gly Ile Gln Gly Pro Ser Gln Glu Ile Ile Gly Gln Leu
            115                 120                 125

Val Gly Glu Asn Ala Ala Glu Arg Arg Val Val Ala Val Val Gly
    130                 135                 140

Ser Gly Gly Ser Gly Lys Thr Thr Leu Ala Lys Gln Val Tyr Glu Lys
145                 150                 155                 160

Ile Arg Cys Gln Phe Ser Cys Ala Ala Phe Val Ser Val Ser Gln Lys
                165                 170                 175

Pro Asn Met Asn Ser Leu Leu Trp Glu Leu Leu Ser Gln Ile Gly Asn
                180                 185                 190

His Gly Gly Asp Leu Gly Met Met Ala Val Gly Tyr Cys Ser Asp Lys
            195                 200                 205

Gln Leu Ile Asp Arg Leu Arg Ser His Leu Glu Lys Gln Arg Tyr Leu
    210                 215                 220

Val Val Ile Asp Asp Val Trp Thr Asn Ser Ala Trp Glu Thr Ile Gln
225                 230                 235                 240

Cys Ala Leu Pro Lys Asn Ala His Ala Ser Lys Ile Ile Leu Thr Thr
                245                 250                 255

Arg Ile Asn Ser Val Gly Gln Phe Ser Cys Thr Pro Asp Glu Gly Phe
                260                 265                 270

Ile Tyr Gln Met Lys Pro Leu Cys Arg Asn Asp Ser Glu Asn Leu Phe
                275                 280                 285

Leu Lys Arg Thr Leu Cys Asp Lys Asp Lys Phe Pro Ala Gln Leu Glu
    290                 295                 300

Gly Ile Lys Asn Glu Ile Ile Glu Lys Cys Asp Gly Leu Pro Leu Ala
305                 310                 315                 320

Ile Val Thr Leu Ala Ser Met Leu Ala Thr Lys Gln Arg Thr Arg Glu
                325                 330                 335

Glu Trp Glu Arg Ala Leu Asp Ser Ile His Ser Met His Lys Lys Asp
                340                 345                 350

Ser Gly Leu Glu Val Met Asp Lys Ile Leu Ser Leu Ser Tyr Arg Asp
                355                 360                 365

Leu Pro His Asn Met Arg Asn Cys Leu Leu Tyr Leu Ser Thr Phe Pro
    370                 375                 380

Glu Asp His Thr Ile Tyr Lys Asp Ala Leu Val Trp Arg Trp Met Ala
385                 390                 395                 400

Glu Gly Phe Ile Ala Glu Thr Gln Gly Phe Thr Leu Glu Gln Val Ala
                405                 410                 415

Glu Gly Tyr Phe Tyr Glu Phe Val Asn Arg Ser Leu Val Gln Pro Ile
                420                 425                 430

Thr Leu Arg Ser Arg Tyr Glu Met Arg Gly Glu Gly Cys Arg Val
                435                 440                 445

His Asp Ile Val Leu Asn Phe Leu Ile Ser Arg Ala Ala Glu Glu Asn
    450                 455                 460

Phe Leu Thr Thr Leu Tyr Gly Ala Gln Gly Val Pro Ser Ser Asp Arg
465                 470                 475                 480

Arg Ile Arg Arg Leu Ser Val Trp Asp Ser Pro Glu His Ala Leu Ala
                485                 490                 495
```

```
Val Ser Arg Ala Thr Met Asn Leu Ser His Leu Arg Ser Val Arg Ile
            500                 505                 510

Cys Asn Val Gly Asp Trp Pro Val Pro Ala Val Leu Asp Leu Pro Val
        515                 520                 525

Leu Arg Val Leu Asp Leu Glu Gly Cys Arg Asp Leu Arg Ile Asp Glu
    530                 535                 540

Pro Asp Cys Ile Leu Ser Leu Phe His Leu Arg Tyr Leu Gly Phe Arg
545                 550                 555                 560

Ser Ala Ser Gly Val Leu Pro Ala Gln Ile Gly Asn Leu His His
                565                 570                 575

Leu Gln Thr Ile Asp Leu Ser Gly Thr Gly Val Thr Gln Leu Pro Glu
            580                 585                 590

Ser Ile Val Gln Leu Lys Arg Leu Met His Leu Val Gly Gln Arg Leu
        595                 600                 605

Ile Met Pro Asp Gly Phe Gly Ser Met Glu Ser Leu Glu Glu Leu Gly
    610                 615                 620

Thr Ile Asp Cys Cys Lys Cys Pro Val Ser Phe Gly Glu Asp Leu Ala
625                 630                 635                 640

Leu Leu Ser Arg Leu Arg Val Leu Arg Val Ala Phe Ile Gly Val Glu
                645                 650                 655

Thr Ser Asp Met Glu Thr Arg Arg Lys Ser Leu Met Ser Ser Leu Cys
            660                 665                 670

Lys Leu Gly Gly Asp Asn Leu Arg Val Thr Ile Asp Leu Ala
        675                 680                 685

Gly Gly Gly Asp Cys Phe Val Glu Ser Trp His Pro Pro Arg Leu
    690                 695                 700

Leu Gln Lys Phe Ile His Ile Ser Gln His Phe Ser Arg Phe Pro Glu
705                 710                 715                 720

Trp Ile Ser Ser Cys Leu Cys Asp Leu Thr His Leu Asp Ile Lys Ala
                725                 730                 735

Glu Lys Met Glu Arg Glu His Leu Ser Val Leu Glu His Leu Pro Ala
            740                 745                 750

Ile Arg Cys Leu Tyr Leu Phe Val Lys Arg Val Ser Glu Asp Gly Leu
        755                 760                 765

Val Ile Ser His Gly Ala Phe Arg Cys Leu Arg Leu Glu Phe Cys
    770                 775                 780

Asn Val Asp Gly Pro Gly Leu Met Phe Ala Gly Val Pro Met Leu
785                 790                 795                 800

Glu Trp Leu Arg Leu Gly Phe Asp Ala Asp Arg Ala Gln Ser Thr Tyr
                805                 810                 815

Gly Gly Leu Glu Val Gly Ile Gln Arg Leu Ser Ser Leu Lys His Val
            820                 825                 830

Val Leu Ile Val Trp Met Val Ser Glu Gly Gly Asp Pro Ala Glu
        835                 840                 845

Gln Ala Val Trp Ser Ala Ile Asn Gly Gln Val Glu Met Leu Pro Asn
    850                 855                 860

Ser Pro Thr Val Asp Ile Arg Phe Arg Arg Ser Gln Leu Gln Ala
865                 870                 875                 880

Ser Ser Glu

<210> SEQ ID NO 5
<211> LENGTH: 2631
<212> TYPE: DNA
<213> ORGANISM: Zea mays
```

<400> SEQUENCE: 5

```
atggagaacc cagacgcgca ggcgaaggcg tgggcggcgg agatgcgcga gctggcctac      60
gacatggagg acagcatcga tctcttcacc caccacgtcg accacgaacc ggccgacacc     120
gccaccaccg cgtcaagag gttcttcctc cggatcatcc ggaagcttaa gaaactccac     180
taccgccaca ggtttgctca ggagatcaaa caactccacg accttgccaa cgaatcgtac     240
cggcgtagga gaggtacag gattgaggag ggcggttcaa gcctcccgca cgcggagatc     300
gatcctcggt tagaggcgct ctacgtggag gtggagaaac tcgtgggcat ccagggccca     360
agccaggaga tcattggaca gctcgtcggc gagaacgcag cggagcggcg gagggttgtc     420
gccgttgttg gatctggagg ttcaggcaag accacacttg ccaaacaggt gtacgagaaa     480
atcaggtgcc aattctcttg tgcagccttt gtgtccgtgt cgcaaaagcc caacatgaat     540
agcctcctgt gggagttgtt atctcaaatc gggaaccatg gtggagattt aggaatgatg     600
gcagtaggat attgcagtga caaacaactg atcgacagac taagatcaca tcttgaaaag     660
cagaggtatc tcgttgtgat agatgatgtt tggacaaact cagcgtggga gaccatacaa     720
tgtgcgctcc ctaaaaatgc ccatgcaagt aaaataattc tgacaacacg aatcaacagt     780
gtaggccagt tctcctgcac tccagatgag ggttttatct atcagatgaa gcctctttgc     840
agaaacgatt ctgaaaatct gtttctgaaa aggacactat gtgataaaga taagtttcct     900
gctcagctgg agggattaa aaacgagata atcgagaaat gcgatggttt gccactggct     960
attgttactc tagctagcat gttagctact aaacagagaa caaggaaga atgggagagg    1020
gcacttgatt caatccattc tacgcacaag aaagatagta gcctggaagt gatggacaag    1080
atactgtctc tgagttacag ggatctacct cacaacatga aaattgctt gctgtatatc    1140
agtacatttc cagaggacca cacgatttac aaagatgctc tagtatggag atggatggct    1200
gaagggttta tcgctgaaac acaaggcttt actttggagc aggttgccga gggctacttc    1260
tacgagtttg tgaacaggag tttggttcag cccataacct tgcgttcaag atatgaaatg    1320
cgtggagaag gaggttgccg agtccatgac attgtactga acttcctcat ctctcgtgca    1380
gctgaagaga actttttaac tacgctgtat ggcgcccagg gggttccatc ttcagaccga    1440
aggattcgcc ggctctctgt ctgggacagt ccagaacacg cactggcagt ctctagagcg    1500
accatgaatc tgtcccatct ccggtcagtt agaaatgca acgttggaga ctggcccgtg    1560
cctgctgttc tagacttacc tgtccttcga gtgttagatc tagagggatg ccgtgatctg    1620
aggatcgtcg accctgactg cattctaagc ttgtttcatc tgaggtacct gggtttccgc    1680
agcgcaagtg gtgtcgtgct accggctcaa ataggaaatt tacaccatct gcagaccatc    1740
gatttaagcg ggactggagt gacacagctg ccagaaagca ttgtccagct caagcgactg    1800
atgcatcttg ttgggcaacg gctcatcatg ccagacgggt tggtagcat ggaatccctt    1860
gaggagttag gtactatcga ctgctgcaag tgccccgctg agggtgctcc gagtgaccga    1920
gtggctttcg tcgggtcga acaagtgac atggaaacca aaggaaatc tttgatgtca    1980
tccctctgca aactcggagg agacaaccctt cggcgtgtca ctattatcga cctcgctggc    2040
ggtgagatt gctttgtgga gtcgtggcac cctcctcctc gtctcctcca gaagttcatc    2100
catatcagtc agcaacagca cttctccagg tttccagaat ggatcagttc ctgcctatgt    2160
gatctcaccc acctggatat aaaggccgaa aagatggaaa gggagcatct aagtgttctt    2220
gaacacctgc ccgccatccg ttatctatac cttttcgtga agcgagtctc cgaagacggg    2280
```

```
ctcgtcatca gccacagcgc gttccgatgt ctacggcgtc tcgagttctg taacttagat    2340
ggacctggtt tgatgtttgc aggaggcgtt ccaatgctgg aatggctgag gctcgggttc    2400
gacgcggata gagcgcaatc gacatacggc ggtctggagg ttggcatcca gcgcctctcg    2460
tctctcaaac atgtcgtgct cattgtctgt atggtttctg aaggcggtga tgatccagcg    2520
gagcaagccg tctggtctgc catcaatggc caagtagaga tgctccccaa ttctccgacg    2580
gttgatatcc ggtttcgtag acggagtcag ctgcaggcaa gctcagaata a             2631
```

<210> SEQ ID NO 6
<211> LENGTH: 876
<212> TYPE: PRT
<213> ORGANISM: Zea mays

<400> SEQUENCE: 6

```
Met Glu Asn Pro Asp Ala Gln Ala Lys Ala Trp Ala Ala Glu Met Arg
1               5                   10                  15

Glu Leu Ala Tyr Asp Met Glu Asp Ser Ile Asp Leu Phe Thr His His
            20                  25                  30

Val Asp His Glu Pro Ala Asp Thr Ala Thr Thr Gly Val Lys Arg Phe
        35                  40                  45

Phe Leu Arg Ile Ile Arg Lys Leu Lys Lys Leu His Tyr Arg His Arg
    50                  55                  60

Phe Ala Gln Glu Ile Lys Gln Leu His Asp Leu Ala Asn Glu Ser Tyr
65                  70                  75                  80

Arg Arg Arg Lys Arg Tyr Arg Ile Glu Glu Gly Gly Ser Ser Leu Pro
                85                  90                  95

His Ala Glu Ile Asp Pro Arg Leu Glu Ala Leu Tyr Val Glu Val Glu
            100                 105                 110

Lys Leu Val Gly Ile Gln Gly Pro Ser Gln Glu Ile Ile Gly Gln Leu
        115                 120                 125

Val Gly Glu Asn Ala Ala Glu Arg Arg Arg Val Val Ala Val Val Gly
    130                 135                 140

Ser Gly Gly Ser Gly Lys Thr Thr Leu Ala Lys Gln Val Tyr Glu Lys
145                 150                 155                 160

Ile Arg Cys Gln Phe Ser Cys Ala Ala Phe Val Ser Val Ser Gln Lys
                165                 170                 175

Pro Asn Met Asn Ser Leu Leu Trp Glu Leu Leu Ser Gln Ile Gly Asn
            180                 185                 190

His Gly Gly Asp Leu Gly Met Met Ala Val Gly Tyr Cys Ser Asp Lys
        195                 200                 205

Gln Leu Ile Asp Arg Leu Arg Ser His Leu Glu Lys Gln Arg Tyr Leu
    210                 215                 220

Val Val Ile Asp Asp Val Trp Thr Asn Ser Ala Trp Glu Thr Ile Gln
225                 230                 235                 240

Cys Ala Leu Pro Lys Asn Ala His Ala Ser Lys Ile Ile Leu Thr Thr
                245                 250                 255

Arg Ile Asn Ser Val Gly Gln Phe Ser Cys Thr Pro Asp Glu Gly Phe
            260                 265                 270

Ile Tyr Gln Met Lys Pro Leu Cys Arg Asn Asp Ser Glu Asn Leu Phe
        275                 280                 285

Leu Lys Arg Thr Leu Cys Asp Lys Asp Lys Phe Pro Ala Gln Leu Glu
    290                 295                 300

Gly Ile Lys Asn Glu Ile Ile Glu Lys Cys Asp Gly Leu Pro Leu Ala
305                 310                 315                 320
```

```
Ile Val Thr Leu Ala Ser Met Leu Ala Thr Lys Gln Arg Thr Arg Glu
                325                 330                 335

Glu Trp Glu Arg Ala Leu Asp Ser Ile His Ser Thr His Lys Lys Asp
                340                 345                 350

Ser Ser Leu Glu Val Met Asp Lys Ile Leu Ser Leu Ser Tyr Arg Asp
                355                 360                 365

Leu Pro His Asn Met Arg Asn Cys Leu Leu Tyr Ile Ser Thr Phe Pro
            370                 375                 380

Glu Asp His Thr Ile Tyr Lys Asp Ala Leu Val Trp Arg Trp Met Ala
385                 390                 395                 400

Glu Gly Phe Ile Ala Glu Thr Gln Gly Phe Thr Leu Glu Gln Val Ala
                405                 410                 415

Glu Gly Tyr Phe Tyr Glu Phe Val Asn Arg Ser Leu Val Gln Pro Ile
                420                 425                 430

Thr Leu Arg Ser Arg Tyr Glu Met Arg Gly Glu Gly Cys Arg Val
                435                 440                 445

His Asp Ile Val Leu Asn Phe Leu Ile Ser Arg Ala Ala Glu Glu Asn
            450                 455                 460

Phe Leu Thr Thr Leu Tyr Gly Ala Gln Gly Val Pro Ser Ser Asp Arg
465                 470                 475                 480

Arg Ile Arg Arg Leu Ser Val Trp Asp Ser Pro Glu His Ala Leu Ala
                485                 490                 495

Val Ser Arg Ala Thr Met Asn Leu Ser His Leu Arg Ser Val Arg Ile
                500                 505                 510

Cys Asn Val Gly Asp Trp Pro Val Pro Ala Val Leu Asp Leu Pro Val
            515                 520                 525

Leu Arg Val Leu Asp Leu Glu Gly Cys Arg Asp Leu Arg Ile Val Asp
            530                 535                 540

Pro Asp Cys Ile Leu Ser Leu Phe His Leu Arg Tyr Leu Gly Phe Arg
545                 550                 555                 560

Ser Ala Ser Gly Val Val Leu Pro Ala Gln Ile Gly Asn Leu His His
                565                 570                 575

Leu Gln Thr Ile Asp Leu Ser Gly Thr Gly Val Thr Gln Leu Pro Glu
            580                 585                 590

Ser Ile Val Gln Leu Lys Arg Leu Met His Leu Val Gly Gln Arg Leu
            595                 600                 605

Ile Met Pro Asp Gly Phe Gly Ser Met Glu Ser Leu Glu Glu Leu Gly
            610                 615                 620

Thr Ile Asp Cys Cys Lys Cys Pro Ala Glu Gly Ala Pro Ser Asp Arg
625                 630                 635                 640

Val Ala Phe Val Gly Val Glu Thr Ser Asp Met Glu Thr Arg Arg Lys
                645                 650                 655

Ser Leu Met Ser Ser Leu Cys Lys Leu Gly Gly Asp Asn Leu Arg Arg
            660                 665                 670

Val Thr Ile Ile Asp Leu Ala Gly Gly Gly Asp Cys Phe Val Glu Ser
            675                 680                 685

Trp His Pro Pro Pro Arg Leu Leu Gln Lys Phe Ile His Ile Ser Gln
            690                 695                 700

Gln Gln His Phe Ser Arg Phe Pro Glu Trp Ile Ser Ser Cys Leu Cys
705                 710                 715                 720

Asp Leu Thr His Leu Asp Ile Lys Ala Glu Lys Met Glu Arg Glu His
                725                 730                 735
```

```
Leu Ser Val Leu Glu His Leu Pro Ala Ile Arg Tyr Leu Tyr Leu Phe
                740                 745                 750

Val Lys Arg Val Ser Glu Asp Gly Leu Val Ile Ser His Ser Ala Phe
            755                 760                 765

Arg Cys Leu Arg Arg Leu Glu Phe Cys Asn Leu Asp Gly Pro Gly Leu
        770                 775                 780

Met Phe Ala Gly Gly Val Pro Met Leu Glu Trp Leu Arg Leu Gly Phe
785                 790                 795                 800

Asp Ala Asp Arg Ala Gln Ser Thr Tyr Gly Gly Leu Glu Val Gly Ile
                805                 810                 815

Gln Arg Leu Ser Ser Leu Lys His Val Val Leu Ile Val Cys Met Val
            820                 825                 830

Ser Glu Gly Gly Asp Asp Pro Ala Glu Gln Ala Val Trp Ser Ala Ile
        835                 840                 845

Asn Gly Gln Val Glu Met Leu Pro Asn Ser Pro Thr Val Asp Ile Arg
850                 855                 860

Phe Arg Arg Arg Ser Gln Leu Gln Ala Ser Ser Glu
865                 870                 875

<210> SEQ ID NO 7
<211> LENGTH: 2667
<212> TYPE: DNA
<213> ORGANISM: Zea mays

<400> SEQUENCE: 7
atggagaacc cagacgcgca ggcgaaggcg tgggcggcgg agatgcgcga gctggcctac      60
gacatggagg acagcatcga tctcttcacc caccacgtcg accacgaacc ggccgacacc     120
gccaccaccg cgtcaagag gttcttcctc cggatcatcc ggaagcttaa gaaactccac     180
taccgccaca ggtttgctca ggagatcaaa caactccacg accttgccaa cgaatcgtac     240
cggcgtagga gaggtacag gattgaggag ggcggttcaa gcctcccgca cgcggagatc     300
gatcctcggt tagaggcgct ctacgtggag gtggagaaac tcgtgggcat ccagggccca     360
agccaggaga tcattggaca gctcgtcggc gagaacgcag cggagcggcg gagggttgtc     420
gccgttgttg gatctggagg ttcaggcaag accacacttg ccaaacaggt gtacgagaaa     480
atcaggtgcc aattctcttg tgcagccttt gtgtccgtgt cgcaaaagcc caacatgaat     540
agcctcctgt gggagttgtt atctcaaatc gggaaccatg gtggagattt aggaatgatg     600
gcagtaggat attgcagtga caaacaactg atcgacagac taagatcaca tcttgaaaag     660
cagagaactg attttcaac tgcttcacaa tctgctctta ggtatctcgt tgtgatagat     720
gatgttggga caaactcagc gtgggagacc atacaatgtg cgctccctaa aaatgcccat     780
gcaagtaaaa taattctgac aacacgaatc aacagtgtag gccagttctc ctgcactcca     840 gatgaggggtt ttatctatca gatgaagcct cttttgcagaa acgattctga aaatctgttt     900
ctgaaaagga cactatgtga taaagataag tttcctgctc agctggaggg gattaaaaac     960
gagataatcg agaaatgcga tggtttgcca ctggctattg ttactctagc tagcatgtta    1020
gctactaaac agagaacaag ggaagaatgg gagagggcac ttgattcaat ccattctacg    1080
cacaagaaag atagtagcct ggaagtgatg acaagatac tgtctctgag ttacagggat    1140
ctacctcaca acatgagaaa ttgcttgctg tatatcagta catttccaga ggaccacacg    1200
atttacaaag atgctctagt atggagatgg atggctgaag ggtttatcgc tgaaacacaa    1260
ggctttactt tggagcaggt tgccgagggc tacttctacg agtttgtgaa caggagtttg    1320
```

```
gttcagccca taaccttgcg ttcaagatat gaaatgcgtg gagaaggagg ttgccgagtc    1380
catgacattg tactgaactt cctcatctct cgtgcagctg aagagaactt tttaactacg    1440
ctgtatggcg cccaggggt tccatcttca daccgaagga ttcgccggct ctctgtctgg     1500
gacagtccag aacacgcact ggcagtctct agagcgacca tgaatctgtc ccatctccgg    1560
tcagttagaa tatgcaacgt tggagactgg cccgtgcctg ctgttctaga cttacctgtc    1620
cttcgagtgt tagatctaga gggatgccgt gatctgagga tcgtcgaccc tgactgcatt    1680
ctaagcttgt ttcatctgag gtacctgggt ttccgcagcg caagtggtgt cgtgctaccg    1740
gctcaaatag gaaatttaca ccatctgcag accatcgatt taagcgggac tggagtgaca    1800
cagctgccag aaagcattgt ccagctcaag cgactgatgc atcttgttgg gcaacggctc    1860
atcatgccag acgggtttgg tagcatggaa tcccttgagg agttaggtac tatcgactgc    1920
tgcaagtgcc ccgctgaggg tgctccgagt gaccgagtgg cttttcgtcgg ggtcgaaaca    1980
agtgacatgg aaaccagaag gaaatctttg atgtcatccc tctgcaaact cggaggagac    2040
aaccttcggc gtgtcactat tatcgacctc gctggcggtg gagattgctt tgtggagtcg    2100
tggcaccctc ctcctcgtct cctccagaag ttcatccata tcagtcagca acagcacttc    2160
tccaggtttc cagaatggat cagttcctgc ctatgtgatc tcacccacct ggatataaag    2220
gccgaaaaga tggaaaggga gcatctaagt gttcttgaac acctgcccgc catccgttat    2280
ctatacctttt tcgtgaagcg agtctccgaa gacgggctcg tcatcagcca cagcgcgttc    2340
cgatgtctac ggcgtctcga gttctgtaac ttagatggac ctggtttgat gtttgcagga    2400
ggcgttccaa tgctggaatg gctgaggctc gggttcgacg cggatagagc gcaatcgaca    2460
tacggcggtc tggaggttgg catccagcgc ctctcgtctc tcaaacatgt cgtgctcatt    2520
gtctgtatgg tttctgaagg cggtgatgat ccagcggagc aagccgtctg gtctgccatc    2580
aatggccaag tagagatgct ccccaattct ccgacggttg atatccggtt tcgtagacgg    2640
agtcagctgc aggcaagctc agaataa                                        2667
```

<210> SEQ ID NO 8
<211> LENGTH: 888
<212> TYPE: PRT
<213> ORGANISM: Zea mays

<400> SEQUENCE: 8

```
Met Glu Asn Pro Asp Ala Gln Ala Lys Ala Trp Ala Ala Glu Met Arg
1               5                   10                  15

Glu Leu Ala Tyr Asp Met Glu Asp Ser Ile Asp Leu Phe Thr His His
            20                  25                  30

Val Asp His Glu Pro Ala Asp Thr Ala Thr Thr Gly Val Lys Arg Phe
        35                  40                  45

Phe Leu Arg Ile Ile Arg Lys Leu Lys Lys Leu His Tyr Arg His Arg
    50                  55                  60

Phe Ala Gln Glu Ile Lys Gln Leu His Asp Leu Ala Asn Glu Ser Tyr
65                  70                  75                  80

Arg Arg Arg Lys Arg Tyr Arg Ile Glu Glu Gly Gly Ser Ser Leu Pro
                85                  90                  95

His Ala Glu Ile Asp Pro Arg Leu Glu Ala Leu Tyr Val Glu Val Glu
            100                 105                 110

Lys Leu Val Gly Ile Gln Gly Pro Ser Gln Glu Ile Ile Gly Gln Leu
        115                 120                 125
```

```
Val Gly Glu Asn Ala Ala Glu Arg Arg Val Val Ala Val Gly
    130                 135                 140

Ser Gly Gly Ser Gly Lys Thr Thr Leu Ala Lys Gln Val Tyr Glu Lys
145                 150                 155                 160

Ile Arg Cys Gln Phe Ser Cys Ala Ala Phe Val Ser Val Ser Gln Lys
                    165                 170                 175

Pro Asn Met Asn Ser Leu Leu Trp Glu Leu Leu Ser Gln Ile Gly Asn
            180                 185                 190

His Gly Gly Asp Leu Gly Met Met Ala Val Gly Tyr Cys Ser Asp Lys
        195                 200                 205

Gln Leu Ile Asp Arg Leu Arg Ser His Leu Glu Lys Gln Arg Thr Asp
    210                 215                 220

Phe Ser Thr Ala Ser Gln Ser Ala Leu Arg Tyr Leu Val Val Ile Asp
225                 230                 235                 240

Asp Val Trp Thr Asn Ser Ala Trp Glu Thr Ile Gln Cys Ala Leu Pro
                245                 250                 255

Lys Asn Ala His Ala Ser Lys Ile Ile Leu Thr Thr Arg Ile Asn Ser
            260                 265                 270

Val Gly Gln Phe Ser Cys Thr Pro Asp Glu Gly Phe Ile Tyr Gln Met
        275                 280                 285

Lys Pro Leu Cys Arg Asn Asp Ser Glu Asn Leu Phe Leu Lys Arg Thr
    290                 295                 300

Leu Cys Asp Lys Asp Lys Phe Pro Ala Gln Leu Glu Gly Ile Lys Asn
305                 310                 315                 320

Glu Ile Ile Glu Lys Cys Asp Gly Leu Pro Leu Ala Ile Val Thr Leu
                325                 330                 335

Ala Ser Met Leu Ala Thr Lys Gln Arg Thr Arg Glu Glu Trp Glu Arg
            340                 345                 350

Ala Leu Asp Ser Ile His Ser Thr His Lys Lys Asp Ser Ser Leu Glu
        355                 360                 365

Val Met Asp Lys Ile Leu Ser Leu Ser Tyr Arg Asp Leu Pro His Asn
    370                 375                 380

Met Arg Asn Cys Leu Leu Tyr Ile Ser Thr Phe Pro Glu Asp His Thr
385                 390                 395                 400

Ile Tyr Lys Asp Ala Leu Val Trp Arg Trp Met Ala Glu Gly Phe Ile
                405                 410                 415

Ala Glu Thr Gln Gly Phe Thr Leu Glu Gln Val Ala Glu Gly Tyr Phe
            420                 425                 430

Tyr Glu Phe Val Asn Arg Ser Leu Val Gln Pro Ile Thr Leu Arg Ser
        435                 440                 445

Arg Tyr Glu Met Arg Gly Glu Gly Gly Cys Arg Val His Asp Ile Val
    450                 455                 460

Leu Asn Phe Leu Ile Ser Arg Ala Ala Glu Glu Asn Phe Leu Thr Thr
465                 470                 475                 480

Leu Tyr Gly Ala Gln Gly Val Pro Ser Ser Asp Arg Arg Ile Arg Arg
                485                 490                 495

Leu Ser Val Trp Asp Ser Pro Glu His Ala Leu Ala Val Ser Arg Ala
            500                 505                 510

Thr Met Asn Leu Ser His Leu Arg Ser Val Arg Ile Cys Asn Val Gly
        515                 520                 525

Asp Trp Pro Val Pro Ala Val Leu Asp Leu Pro Val Leu Arg Val Leu
    530                 535                 540
```

| | | | | | | | | | | | |
|---|---|---|---|---|---|---|---|---|---|---|---|
| Asp | Leu | Glu | Gly | Cys | Arg | Asp | Leu | Arg | Ile | Val | Asp | Pro | Asp | Cys | Ile |
| 545 | | | | | 550 | | | | | 555 | | | | | 560 |

Asp Leu Glu Gly Cys Arg Asp Leu Arg Ile Val Asp Pro Asp Cys Ile
545                 550                 555                 560

Leu Ser Leu Phe His Leu Arg Tyr Leu Gly Phe Arg Ala Ser Gly
            565                 570                 575

Val Val Leu Pro Ala Gln Ile Gly Asn Leu His His Leu Gln Thr Ile
            580                 585                 590

Asp Leu Ser Gly Thr Gly Val Thr Gln Leu Pro Glu Ser Ile Val Gln
            595                 600                 605

Leu Lys Arg Leu Met His Leu Val Gly Gln Arg Leu Ile Met Pro Asp
610                 615                 620

Gly Phe Gly Ser Met Glu Ser Leu Glu Glu Leu Gly Thr Ile Asp Cys
625                 630                 635                 640

Cys Lys Cys Pro Ala Glu Gly Ala Pro Ser Asp Arg Val Ala Phe Val
            645                 650                 655

Gly Val Glu Thr Ser Asp Met Glu Thr Arg Arg Lys Ser Leu Met Ser
            660                 665                 670

Ser Leu Cys Lys Leu Gly Gly Asp Asn Leu Arg Arg Val Thr Ile Ile
            675                 680                 685

Asp Leu Ala Gly Gly Gly Asp Cys Phe Val Glu Ser Trp His Pro Pro
690                 695                 700

Pro Arg Leu Leu Gln Lys Phe Ile His Ile Ser Gln Gln Gln His Phe
705                 710                 715                 720

Ser Arg Phe Pro Glu Trp Ile Ser Ser Cys Leu Cys Asp Leu Thr His
            725                 730                 735

Leu Asp Ile Lys Ala Glu Lys Met Glu Arg Glu His Leu Ser Val Leu
            740                 745                 750

Glu His Leu Pro Ala Ile Arg Tyr Leu Tyr Leu Phe Val Lys Arg Val
            755                 760                 765

Ser Glu Asp Gly Leu Val Ile Ser His Ser Ala Phe Arg Cys Leu Arg
            770                 775                 780

Arg Leu Glu Phe Cys Asn Leu Asp Gly Pro Gly Leu Met Phe Ala Gly
785                 790                 795                 800

Gly Val Pro Met Leu Glu Trp Leu Arg Leu Gly Phe Asp Ala Asp Arg
            805                 810                 815

Ala Gln Ser Thr Tyr Gly Gly Leu Glu Val Gly Ile Gln Arg Leu Ser
            820                 825                 830

Ser Leu Lys His Val Val Leu Ile Val Cys Met Val Ser Glu Gly Gly
            835                 840                 845

Asp Asp Pro Ala Glu Gln Ala Val Trp Ser Ala Ile Asn Gly Gln Val
850                 855                 860

Glu Met Leu Pro Asn Ser Pro Thr Val Asp Ile Arg Phe Arg Arg Arg
865                 870                 875                 880

Ser Gln Leu Gln Ala Ser Ser Glu
            885

<210> SEQ ID NO 9
<211> LENGTH: 2930
<212> TYPE: DNA
<213> ORGANISM: Zea mays

<400> SEQUENCE: 9
atggagaacc cagacgcgca ggcgaaggcg tgggcggcgg agatgcgcga gctggcctac      60
gacatggagg acagcatcga tctcttcacc caccacgtcg accacgaacc ggccgacacc     120
gccaccaccg gcgtcaagag gttcttcctc cggatcatcc ggaagcttaa gaaactccac     180

```
taccgccaca ggtttgttca ggagatcaaa caactccacg accttgccaa cgaatcgtac    240
cggcgtagga agaggtacag gattgaggag ggcggttcaa gcctctcgca cgcggagatc    300
gatcctcggt tagaggcgct ctacgtggag gtggagaaac tcgtgggcat ccagggccca    360
agccaggaga tcattggaca gctcgtcggc gagaacgcag cggagcgacg gagggttgtc    420
gccgttgttg gatctggagg ttcaggcaag accacacttg ccaaacaggt gtacgagaaa    480
atcaggtgcc aattctcttg tgcagccttt gtgtctgtgt cgcaaaagcc caacatgaat    540
agcctcctgt gggagttgct atctcaaatc gggaaccatg gtggagattt aggaatgatg    600
gcagtaggat attgcagtga caacaactg atcgacagac taagatcaca tcttgaaaag     660
cagaggttag tttaccttt cattccggtt agcttaattc ggtacaccaa ctagagattt     720
gtgatttgct attaattaca ccaaatttct cctacacaac aataactggt ttagcatgat    780
ggcgatccaa agtcaaaact atcttctact actagtgtat gccatactca tatagatatt    840
ttcttttcat aaactctcgt agcatttta catgcattca tattcctatt gcctttatac     900
agaactgatt tttcactgct tcacaatctg ctcttaggta tctcgttgtg atagatgatg    960
tttggacaaa ctcagcgtgg gagaccatac aatgtgcgct ccctaaaaat gcccatgcaa    1020
gtaaaataat tctgacaaca cgaatcaaca gtgtaggcca gttctcctgc actccagatg    1080
agggttttat ctatcagatg aagcctcttt gcagaaacga ttctgaaaat ctgtttctga    1140 aaggacact atgtgataaa gataagtttc ctgctcagct ggagggatt aaaaacgaga       1200 taatcgagaa atgcgatggt ttgccactgg ctattgttac tctagctagc atgttagcta    1260
ctaaacagag aacaagggaa gaatgggaga gggcacttga ttcaatccat tctatgcaca    1320
agaaagatag tggcctggaa gtgatggaca agatactgtc tctgagttac agggatctac    1380
ctcacaacat gagaaattgc ttgctgtatc tcagtacatt tccagaggac cacacgattt    1440
acaaagatgc cctagtatgg agatggatgg ctgaagggtt tatcgctgaa acacaaggct    1500
ttactttgga gcaggttgcc gagggctact tctacgagtt tgtgaacagg agtttggttc    1560
agcccataac cttgcgttca agatatgaaa tgcgtggaga aggaggttgc cgagtccatg    1620
acattgtact gaacttcctc atctctcgtg cagctgaaga gaacttttta actacgctgt    1680
atggcgccca gggggttcca tcttcagacc gaaggattcg ccggctctct gtctgggaca    1740
gtccagaaca cgcactggca gtctctagag cgaccatgaa tctgtcccat ctccggtcag    1800
ttagaatatg caacgttgga gactggcccg tgcctgctgt tctagactta cctgtccttc    1860
gagtgttaga tctagaggga tgccgtgatc tgaggatcga cgaacctgac tgcattctaa    1920
gcttgtttca tctgagatac ctgggttttcc gcagcgcaag tggtgtcgtg ctaccggctc    1980
aaatcggaaa tttacaccat ctgcagacca tcgatttaag cgggactgga gtgacacagc    2040
tgccagaaag cattgtccag ctcaagcgac tgatgcatct tgttgggcaa cggctcatca    2100
tgccagacgg gttggtagc atggaatccc ttgaggagtt aggtactatc gactgctgca    2160
agtgccccgt cagttttggg gaagacctag cacttctgag caggctgagg gtgctccgag    2220
tggctttcat cggggtcgaa acaagtgaca tggaaaccag aaggaaatct ttgatgtcat    2280
ccctctgcaa actcggagga gacaaccttc ggcgtgtcac tattatcgac ctcgctggcg    2340
gtggagattg ctttgtggag tcgtggcacc ctcctcctcg tctcctccag aagttcatcc    2400
atatcagtca gcaacagcac ttctccaggt ttccagaatg gatcagttcc tgcctatgtg    2460
atctcaccca cctggatata aaggccgaaa agatggaaag ggagcatcta agtgttcttg    2520
```

```
aacacctgcc cgccatccgt tgcctatacc ttttcgtgaa gcgagtctcc gaagacgggc   2580
tcgccatcag ccacggcgcg ttccgatgtc tacggcgtct cgagttctgc aacgtagatg   2640
gacctggttt tgatgtttgca ggaggcgttc caatgttgga atggctgagg ctcgggttcg   2700
acgcggatag agcgcaatcg acatacggcg gtctggaggt tggcatccag cgcctctcgt   2760
ctctcaaaca tgtcgtgctc attgtatgga tggtttctga aggcggtgat gatccagcgg   2820
agcaagccgt ctggtctgcc atcaatggcc aagtagagat gctccccaac tctccgacgg   2880
ttgatatccg gtttcgtaga cggagtcagc tgcaggcaag ctcagaataa                 2930
```

<210> SEQ ID NO 10
<211> LENGTH: 16
<212> TYPE: PRT
<213> ORGANISM: Zea mays

<400> SEQUENCE: 10

```
Val Ser Phe Gly Glu Asp Leu Ala Leu Leu Ser Arg Leu Arg Val Leu
1               5                   10                  15
```

<210> SEQ ID NO 11
<211> LENGTH: 667
<212> TYPE: PRT
<213> ORGANISM: Zea mays

<400> SEQUENCE: 11

```
Met Ala Ala His Gln Pro His Leu Ser Val Leu Leu Val Leu Leu
1               5                   10                  15

Ala Ala His Val Val Ser Thr Ser Ala His Gly Glu Pro Pro Leu Pro
                20                  25                  30

Ser Pro Tyr Asn Thr Ser Ala His Gly Glu Pro Pro Leu Pro Ser Thr
            35                  40                  45

Tyr Asn Ala Ser Met Cys Ser Ser Phe Trp Cys Gly Val Glu Ile
        50                  55                  60

Arg Tyr Pro Phe Tyr Leu Ala Asn Ala Ile Ala Asp Tyr Ser Gly Ser
65                  70                  75                  80

Tyr Tyr Ser Cys Gly Tyr Thr Asp Leu Ser Val Ser Cys Glu Leu Glu
                85                  90                  95

Val Glu Gly Ser Pro Thr Thr Trp Thr Pro Thr Ile Arg Leu Gly Gly
            100                 105                 110

Gly Asp Tyr Thr Val Lys Asn Ile Ser Tyr Leu Tyr Asp Gln Gln Thr
        115                 120                 125

Ile Ser Leu Ala Asp Arg Asp Val Leu Gly Gly Gly Cys Pro Val
    130                 135                 140

Val Arg His Asn Val Ser Phe Asp Glu Thr Trp Leu His Leu His Asn
145                 150                 155                 160

Ala Ser Ala Phe Asp Asn Leu Thr Phe Phe Gly Cys His Trp Gly
                165                 170                 175

Pro Arg Asn Thr Pro Pro Glu Phe Ala Asp Tyr Asn Ile Ser Cys Ala
            180                 185                 190

Gly Phe Asn Thr Pro Thr Ile Ser Gly Gly Arg Ser Phe Val Phe Lys
        195                 200                 205

Thr Gly Asp Leu Asp Glu Gln Glu Glu Gln Glu Leu Ala Leu His Cys
    210                 215                 220

Asp Glu Val Phe Ser Val Pro Val Arg Arg Asp Ala Leu Gln Ala Ile
225                 230                 235                 240
```

```
Val Ser Asn Phe Ser Leu Thr Arg Asp Gly Tyr Gly Glu Val Leu Arg
                245                 250                 255

Gln Gly Phe Glu Leu Glu Trp Asn Arg Thr Ser Glu Asp Gln Cys Gly
                260                 265                 270

Arg Cys Glu Gly Ser Gly Ser Gly Gly Trp Cys Ala Tyr Ser Gln Lys
            275                 280                 285

Arg Glu Phe Leu Gly Cys Leu Cys Ser Gly Gly Lys Val Gly Ser Pro
        290                 295                 300

Phe Cys Lys Pro Ser Arg Ser Lys Arg Lys Glu Gly Pro Ile Val Gly
305                 310                 315                 320

Ala Val Ala Val Ala Phe Leu Cys Leu Val Ile Leu Thr Cys Phe Leu
                325                 330                 335

Ala Cys Arg His Gly Ser Leu Pro Phe Lys Ser Glu Asn Lys Pro Gly
                340                 345                 350

Thr Arg Ile Glu Ser Phe Leu Gln Lys Asn Glu Ser Ile His Pro Lys
                355                 360                 365

Arg Tyr Thr Tyr Ala Asp Val Lys Arg Met Thr Lys Ser Phe Ala Val
            370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
                420                 425                 430

Val Asn Val Val Thr Leu Leu Gly Phe Cys Leu Gln Gly Ser Lys Arg
            435                 440                 445

Ala Leu Ile Tyr Glu Tyr Met Pro Asn Gly Ser Leu Glu Arg Tyr Ala
        450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
                500                 505                 510

Leu Leu Asp Gln Asp Phe Cys Pro Lys Ile Ser Asp Phe Gly Leu Ala
            515                 520                 525

Lys Leu Cys Leu Asn Lys Glu Ser Ala Ile Ser Ile Ala Gly Ala Arg
        530                 535                 540

Gly Thr Ile Gly Tyr Ile Ala Pro Glu Val Tyr Ser Lys Gln Phe Gly
545                 550                 555                 560

Ile Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
                580                 585                 590

Ser Ser Gln Tyr Phe Pro Gln Trp Leu Tyr Glu His Leu Asp Asp Tyr
            595                 600                 605

Cys Val Gly Ala Ser Glu Ile Asn Gly Glu Thr Thr Glu Leu Val Arg
        610                 615                 620

Lys Met Ile Val Val Gly Leu Trp Cys Ile Gln Val Ile Pro Thr Asp
625                 630                 635                 640

Arg Pro Thr Met Thr Arg Val Val Glu Met Leu Glu Gly Ser Thr Ser
                645                 650                 655
```

Asn Leu Glu Leu Pro Pro Arg Val Leu Leu Ser
            660                 665

<210> SEQ ID NO 12
<211> LENGTH: 666
<212> TYPE: PRT
<213> ORGANISM: Zea mays

<400> SEQUENCE: 12

Met Ala Ala His Leu Pro Arg Leu Pro Val Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
            35                  40                  45

Tyr Asn Val Ser Met Cys Ser Glu Ser Phe Trp Cys Gly Gly Val Glu
        50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
            85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
            115                 120                 125

Ser Leu Ala Asp Ser Asp Val Leu Gly Gly Gly Glu Cys Pro Val Val
            130                 135                 140

His His Asn Val Ser Phe Asp Glu Thr Trp Leu His Asn Pro Ser Ala
145                 150                 155                 160

Phe Asp Asn Leu Thr Phe Phe Gly Cys His Trp Gly Pro Arg Asp
            165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
            195                 200                 205

Leu Asp Glu His Ala Glu Gln Glu Leu Ala Ser His Cys Asp Glu Val
            210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
            245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
            275                 280                 285

Leu Gly Cys Leu Cys Ser Gly Gly Lys Ala Gly Asn Pro Phe Cys Lys
            290                 295                 300

Pro Ser Arg Ser Lys Arg Lys Glu Ala Ser Ile Val Gly Ala Val Ala
305                 310                 315                 320

Val Ala Phe Leu Cys Leu Val Ile Leu Thr Cys Phe Leu Ala Cys Arg
            325                 330                 335

His Gly Ser Leu Pro Phe Lys Ser Glu Asn Lys Pro Gly Thr Arg Ile
            340                 345                 350

-continued

```
Glu Ser Phe Leu Gln Lys Asn Glu Ser Ile His Pro Lys Arg Tyr Thr
        355                 360             365

Tyr Thr Asp Val Lys Arg Met Thr Lys Ser Phe Ala Val Lys Leu Gly
    370             375             380

Gln Gly Gly Phe Gly Ala Val Tyr Lys Gly Ser Leu His Asp Gly Arg
385             390             395             400

Gln Val Ala Val Lys Met Leu Lys Asp Thr Gln Gly Asp Gly Glu Glu
            405             410             415

Phe Met Asn Glu Val Ala Ser Ile Ser Arg Thr Ser His Val Asn Val
            420             425             430

Val Thr Leu Leu Gly Phe Cys Leu Gln Gly Ser Lys Arg Ala Leu Ile
        435             440             445

Tyr Glu Tyr Met Pro Asn Gly Ser Leu Glu Arg Tyr Ala Phe Thr Gly
    450             455             460

Asp Met Asn Ser Glu Asn Leu Leu Thr Trp Glu Arg Leu Phe Asp Ile
465             470             475             480

Ala Ile Gly Thr Ala Arg Gly Leu Glu Tyr Leu His Arg Gly Cys Asn
            485             490             495

Thr Arg Ile Val His Phe Asp Ile Lys Pro His Asn Ile Leu Leu Asp
            500             505             510

Gln Asp Phe Cys Pro Lys Ile Ser Asp Phe Gly Leu Ala Lys Leu Cys
        515             520             525

Leu Asn Lys Glu Ser Ala Ile Ser Ile Val Gly Ala Arg Gly Thr Ile
    530             535             540

Gly Tyr Ile Ala Pro Glu Val Tyr Ser Lys Gln Phe Gly Thr Ile Ser
545             550             555             560

Ser Lys Ser Asp Val Tyr Ser Tyr Gly Met Met Val Leu Glu Met Val
            565             570             575

Gly Ala Arg Glu Arg Asn Thr Ser Ala Ser Ala Asp Ser Asp His Ser
            580             585             590

Ser Gln Tyr Phe Pro Gln Trp Ile Tyr Glu His Leu Asp Asp Tyr Cys
        595             600             605

Val Gly Ala Ser Glu Ile Asn Gly Glu Thr Thr Glu Leu Val Arg Lys
    610             615             620

Met Ile Val Val Gly Leu Trp Cys Ile Gln Val Ile Pro Thr Asp Arg
625             630             635             640

Pro Thr Met Thr Arg Val Val Glu Met Leu Glu Gly Ser Thr Ser Asn
            645             650             655

Leu Glu Leu Pro Pro Arg Val Leu Leu Ser
            660             665
```